United States Patent [19]

Rosenfeld

[11] Patent Number: 5,957,859
[45] Date of Patent: Sep. 28, 1999

[54] METHOD AND SYSTEM FOR DETECTION OF DECEPTION USING SCALED P300 SCALP AMPLITUDE DISTRIBUTION

[75] Inventor: J. Peter Rosenfeld, Winnetka, Ill.

[73] Assignee: J. Peter Rosenfeld Ph.D., Glencoe, Ill.

[21] Appl. No.: 08/901,617

[22] Filed: Jul. 28, 1997

[51] Int. Cl.⁶ .................................................... A61B 5/04
[52] U.S. Cl. .......................................... 600/544; 128/898
[58] Field of Search .................................... 600/544, 545, 600/546; 128/898, 920

[56] References Cited

U.S. PATENT DOCUMENTS

| | | |
|---|---|---|
| 4,736,751 | 4/1988 | Gevins et al. . |
| 4,932,416 | 6/1990 | Rosenfeld . |
| 5,406,956 | 4/1995 | Farwell . |
| 5,450,855 | 9/1995 | Rosenfeld . |
| 5,467,777 | 11/1995 | Farwell . |
| 5,564,433 | 10/1996 | Thornton . |
| 5,622,181 | 4/1997 | Rosenfeld . |
| 5,752,922 | 5/1998 | Rosenfeld . |
| 5,762,611 | 6/1998 | Lewis et al. . |
| 5,797,853 | 8/1998 | Musha et al. . |
| 5,846,207 | 12/1998 | Rosenfeld . |
| 5,857,979 | 1/1999 | Ryu et al. . |

OTHER PUBLICATIONS

J.W. Ellwanger et al., Revised, Combined Oddball and Matching–To–Sample Procedure for Detection of Simulated Cognitive Deficit with P300: Deception–Specific Amplitude Distributions; SPR meeting, Oct. 1996.

*Primary Examiner*—George Manuel
*Assistant Examiner*—Shawna J. Shaw
*Attorney, Agent, or Firm*—Brinks Hofer Gilson & Lione

[57] ABSTRACT

A method and system for testing for untruthfulness in a subject. In a testing session, at least one test stimulus is presented to the subject. The subject's brain waves are sensed from at least two locations of the subject's scalp to obtain a scaled distribution representing the subject's response to the at least one test stimulus. The distribution obtained in response to the test stimulus is compared to a similarly scaled control distribution of the subject's brain waves. The control distribution represents the brain waves sensed from the at least two locations of the subject's scalp in response to a control stimulus. The subject's truthfulness in response to the at least one test stimulus is inferred from the comparison.

40 Claims, 10 Drawing Sheets

METHOD AND SYSTEM FOR DETECTION OF DECEPTION USING SCALED P300 SCALP AMPLITUDE DISTRIBUTION

BACKGROUND OF THE INVENTION

The present invention relates to a method and apparatus for the detection of deception.

Detection of deception has importance in many fields. There are obvious applications for detection of deception in law enforcement. Employment screening is another area in which there is need for a reliable means for detection of deception. Other areas in which detection of deception has utility include the screening of insurance or medical claims.

For example, claims of amnesia are frequently raised in a variety of legal situations. Amnesia may be easily feigned, and it is difficult, if not impossible to identify. Neuropsychologists have been used to attempt diagnosis and provide expert testimony in personal injury litigation cases involving such claims. A vital concern is their ability to distinguish between actual and exaggerated impairment. In many cases, their capability to detect feigned impairment is limited.

Tests have been devised to detect memory deficit malingering. The Hiscock Forced Choice Procedure (FCP) is such a test (See, Hiscock, M., & Hiscock, C. K. , Refining the forced-choice method for detection of malingering. *Journal of Clinical and Fxperimental Neuropsychology*, 11, 967–974 (1989)). This procedure is a simple delayed matching-to-sample task using multi-digit numbers. An increasingly long interval between sample and test numbers may make the test appear difficult, but in actuality, task difficulty is low and recognition of the first digit alone is sufficient for correct response. Normals and non-litigating patients with mild to moderate head injury perform at a rate of 100% correct, typically, on this relatively easy test.

It has been demonstrated that brain waves, in particular the P300 event-related potential (ERP), can be used successfully in detection of deception and malingering. This has been described in U.S. Pat. Nos. 4,932,416, 5,113,870, 5,137,027, and 5,622,181 (the disclosures of which are incorporated by reference herein) and in publications by Towle, V. T., Sutcliffe, & Sokol, S., Diagnosing functional visual deficits with the P300 component of the visual evoked potential, *Archives of Opthalmology*, 103, 47–50 (1985); Rosenfeld, J. P., Nasman, V. T., Whalen, R., Cantwell, B., & Mazzeri, J., Late vertex positivity in event-related potentials as a guilty knowledge indicator. A new method of lie detection. *International Journal of Neuroscience*, 34, 125–129 (1987); Rosenfeld, J. P., Cantwell, G., Nasman, V. T., Wojdac, V. Ivanov, S., & Mazzeri, L., A modified, event-related potential-based guilty knowledge test, *International Journal of Neuroscience*, 24, 157–161(1988); Rosenfeld, J. P., Angell, A., Johnson, M., & Qian, J., An ERP-based, control-question lie detector analog: Algorithms for discriminating effects within individuals' average waveforms. *Psychophysiology*, 38, 319–335 (1991); Rosenfeld, J. P., Sweet, J. J., Chuang, J., Ellwanger, J & Song, L., Detection of simulated malingering using forced choice recognition enhanced with event-related potential recording, *The Clinical Neuropsychologist*, 10, 163–179 (1996); Farwell, L. A., & Donchin, E., The truth will out: Interrogative polygraphy ("lie detection") with event-related potentials, *Psychophysiology*, 28, 531–547 (1991); Allen, J., Iacono, W. G. and Danielson, K. D., The identification of concealed memories using the event-related potential and implicit behavioral measures: A methodology for prediction in the face of individual differences, *Psychophysiology*, 29, 504–522 (1992); and Ellwanger, J., Rosenfeld, J. P. Sweet, J. J. & Bhatt, M., Detecting simulated amnesia for autobiographical and recently learned information using the P300 event-related potential, *International Journal of Psychophysiology*, 23, 9–23 (1996).

In these studies, the P300 component measured at the Pz locus has been the basic dependent variable analyzed. While such approaches have yielded up to about 90% accuracy in detecting guilt or innocence, there still remains a need to provide a means for detection of deception that is more reliable.

SUMMARY OF THE INVENTION

The present invention comprises a method and system for testing for untruthfulness in a subject as well as for classifying different types of deceptions. In a testing session, at least one test stimulus is presented to the subject. The subject's brain waves are sensed from at least two locations of the subject's scalp then scaled so as to obtain a scaled distribution representing the subject's response to the at least one test stimulus. The distribution obtained in response to the at least one test stimulus is compared to a control distribution. The control distribution a similarly scaled distribution of the subject's brain waves sensed from the at least two locations of the subject's scalp in response to a control stimulus. The control stimulus represents something to which the subject's truthful response is known. The subject's truthfulness or untruthfulness in response to the at least one test stimulus is inferred from the comparison.

MFTRU=Match Frequent, Malinger; and MFMAL=Match Frequent, Malinger.

Figure 9:
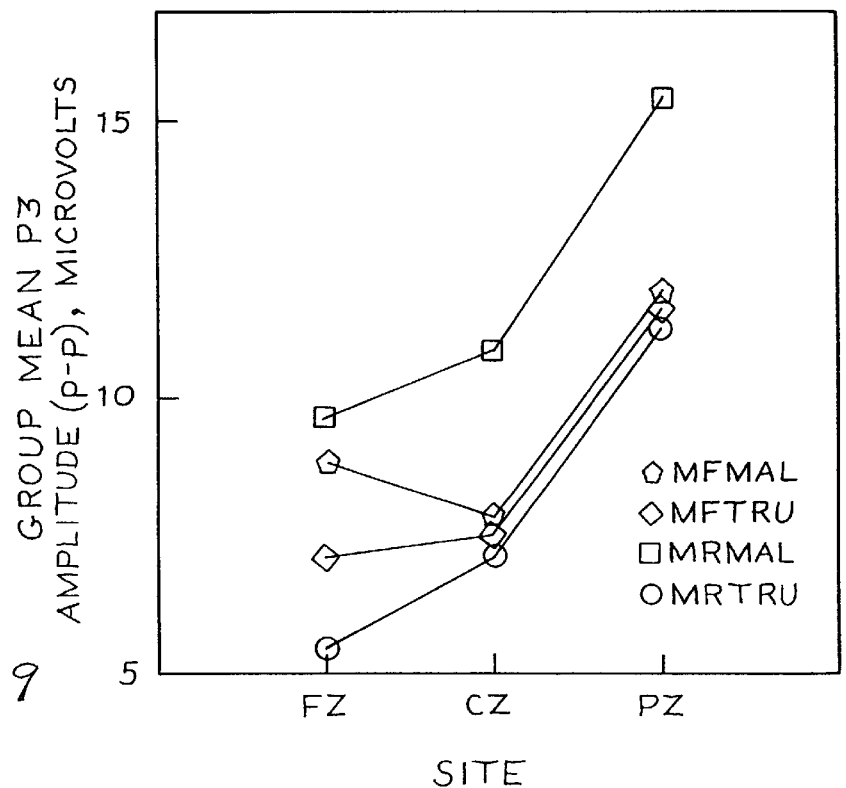

FIG. 9 is a diagram plotting group mean P3 amplitude (p-p), μV, P3FCP, where MRTRU=Match Rare, Truth; MRMAL=Match Rare, Malinger;

MFTRU=Match Frequent, Truth; and MFMAL=Match Frequent, Malinger.

Figure 10:
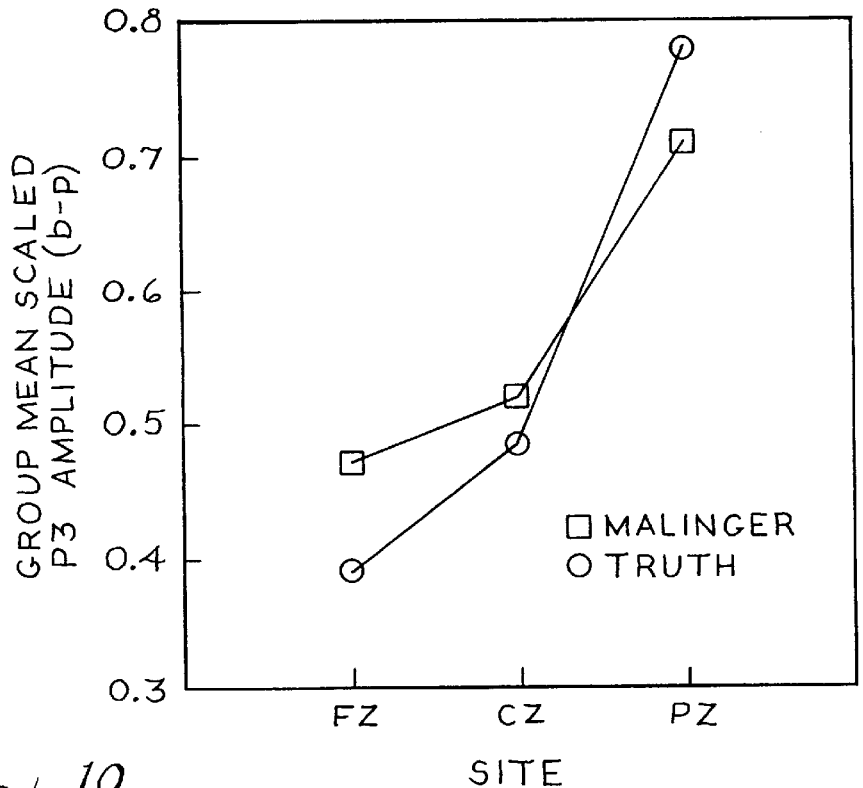

FIG. 10 is a diagram plotting group mean scaled P3 amplitude, Truth vs. Malinger (b-p), PFCP.

Figure 11:
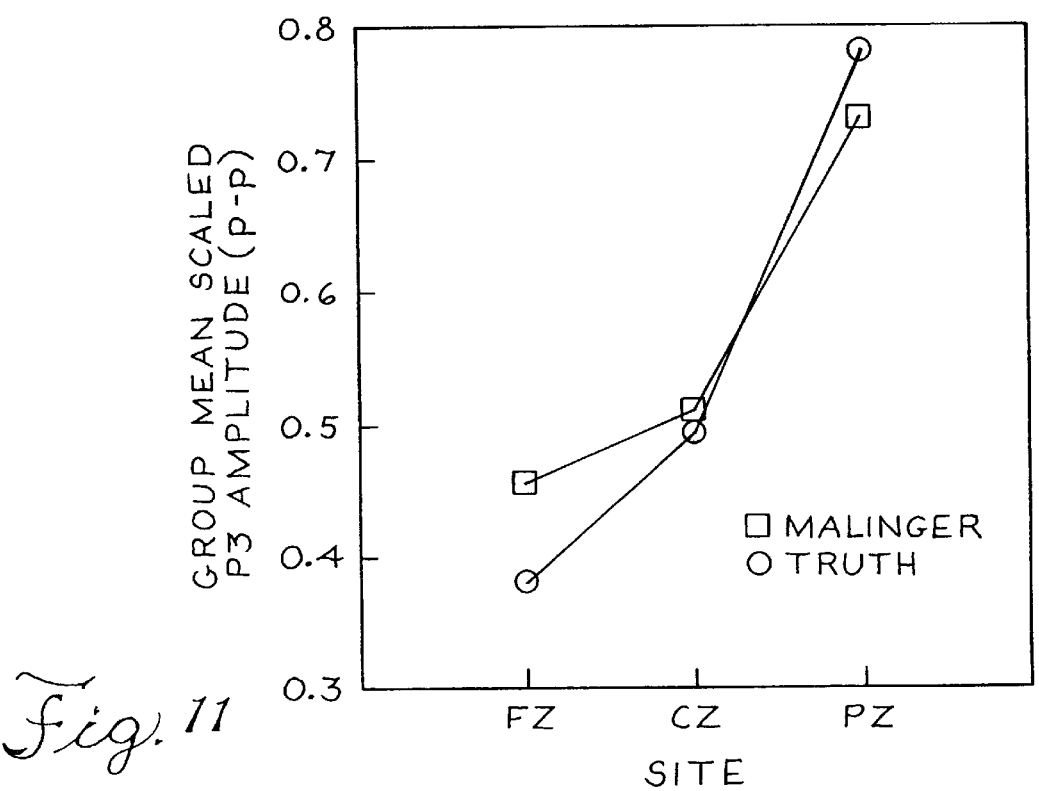

FIG. 11 is a diagram plotting group mean scaled P3 amplitude, Truth vs. Malinger (p-p) P3FCP.

Figure 12:
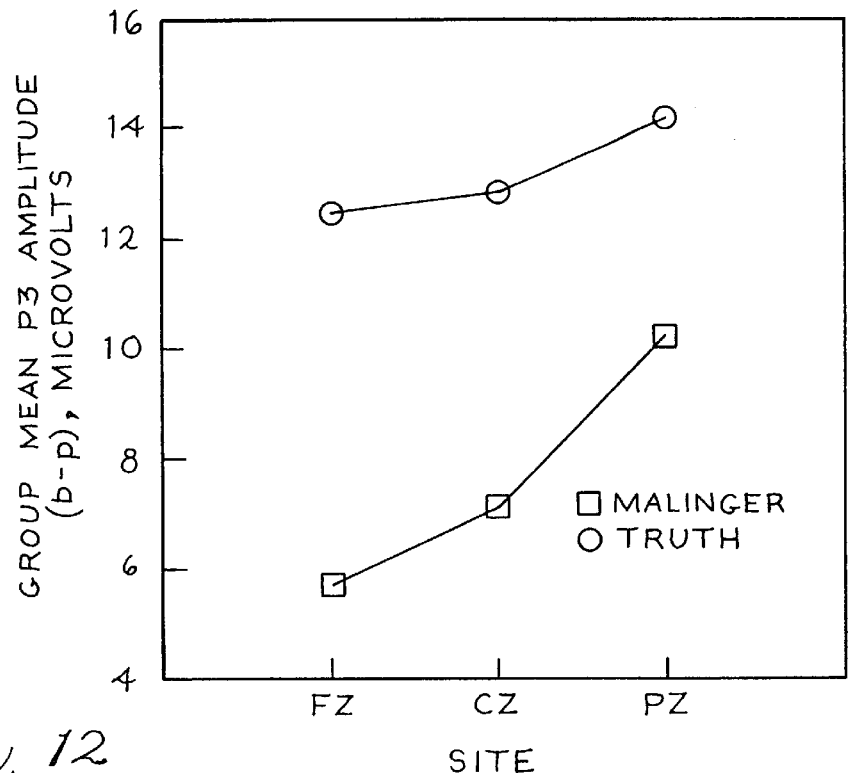

FIG. 12 is a diagram plotting group mean P3 amplitude (b-p) μV, Birthday.

Figure 13:
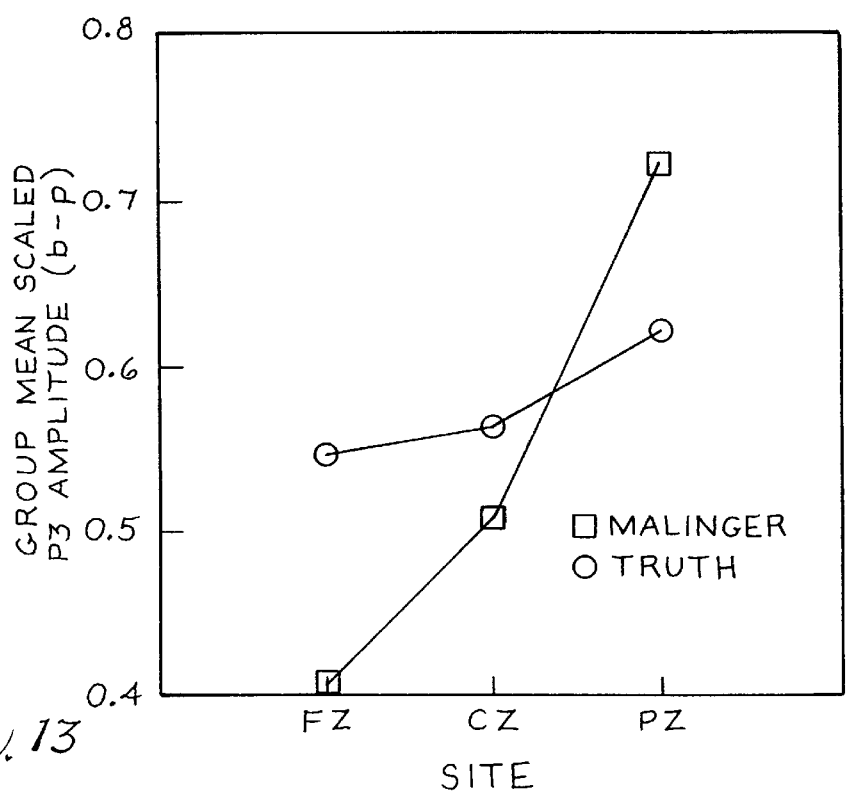

FIG. 13 is a diagram plotting group mean scaled P3 amplitude (b-p), Truth vs. Malinger, Birthday.

Figure 14:
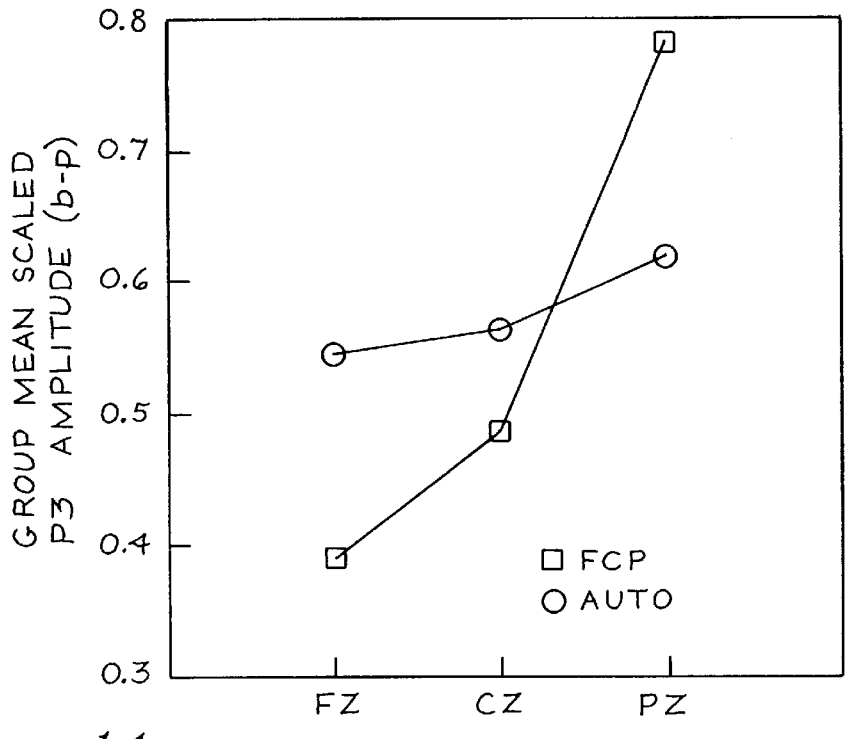

FIG. 14 is a diagram plotting group mean scaled P3 amplitude (b-p), Truth P3FCP vs. Truth Birthday.

Figure 15:
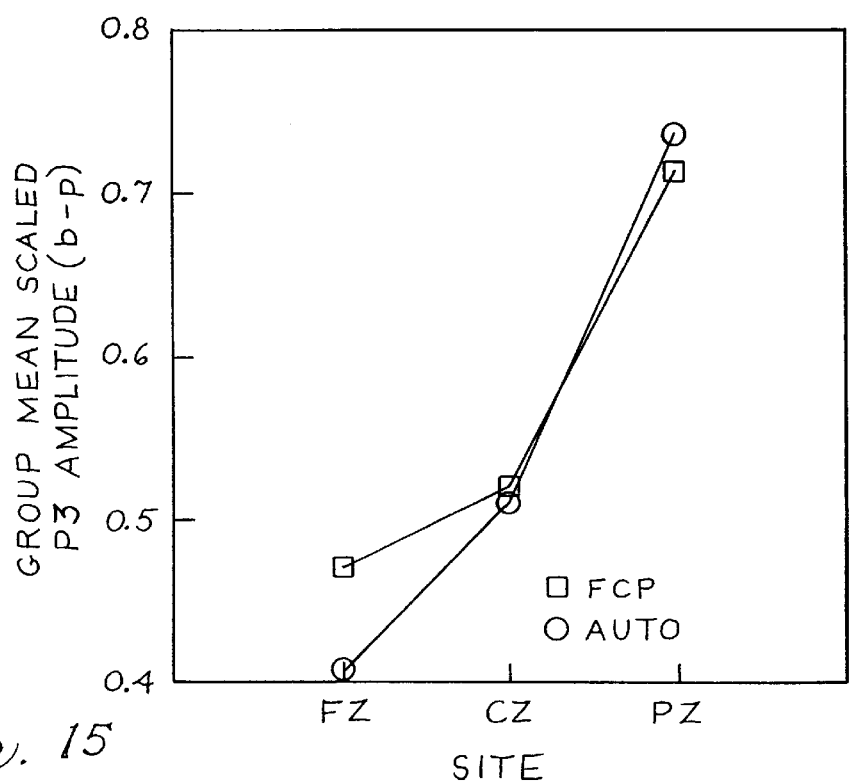

FIG. 15 is a diagram plotting group mean scaled P3 amplitude (b-p), and Malinger P3FCP vs. Malinger Birthday.

Figure 16:
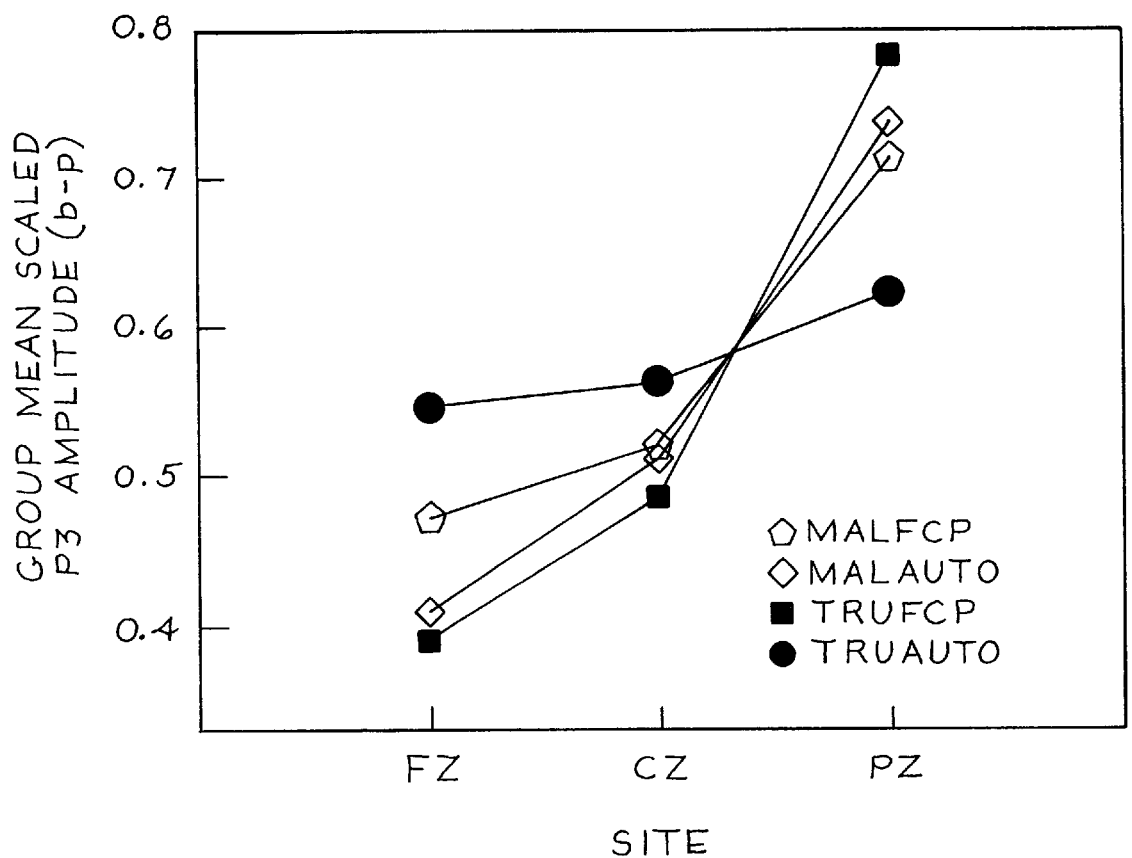

FIG. 16 is a diagram plotting group mean scaled P3 amplitude (b-p), Truth P3FCP, Truth, Birthday, Malinger P3FCP Malinger Birthday.

DETAILED DESCRIPTION OF THE PRESENTLY PREFERRED EMBODIMENTS

I. GENERAL

The present invention relates to a method for detection of deception based on observation of statistically confirmed interactions of response (truth-telling vs. deceptive) and site in scaled brain wave amplitude data. Although brain wave amplitude and in particular the P300 event-related potential (ERP) amplitude from a single site have been used previously for detection of deception, there has been no diagnostic use of date from multiple recording sites, and in particular scaled amplitudes from-multiple sites. As disclosed herein, there is a novel dependent variable in the ERP domain made available by looking at the scalp distribution of the P300 amplitude. The shaper profile of the P300 distribution has been observed to differ between deceptive and truth-telling conditions. Scaled scalp distribution of P300, apart from unscaled amplitude at any one or more sites, can be used to differentiate deception and truth-telling in individuals.

P300 is an event related brain EEG potential evoked by meaningful and rare stimuli. In the patents cited above, it is described how to use P300, EEG, and ERPs. These previous patents disclosed how it is possible to utilize the amplitude of the P300 ERP recorded at one (Pz) site, or averaged across several sites, as a deception index. For example, U.S. Pat. No. 5,622,181, described a procedure wherein a subject is presented with a series of sample numbers, each followed after some delay, by either a match (R) or a mismatch (W). The subject declares whether the sample numbers are a R or a W. Malingering (deceptive) subjects may lie on a large proportion of trials, yielding scores of <60% right. This suggests that verbally they cannot tell a mismatch from a match. However, it is found that their P300 amplitudes at Pz are larger to R than to W, thus undermining their claim of cognitive deficit: Their brains can tell the difference between R and W, even though the subject in effect claims he/she cannot.

If a subject performs two different kinds of P300-evoking tasks (or is subjected to two different P300-evoking conditions) which generate two different distributions of scaled amplitude at various scalp sites, it is likely that the two tasks have differing sets of neural generators (neurons) with differing locations in brain. Thus one plots scaled amplitude separately for each task (condition) as a function of scalp site, and if one can show that the scaled curves are not parallel, the tasks involve differing neurogenerator sets in brain.

In accordance with an embodiment of the present invention, deception is identified as one condition and truth-telling as another. In accordance with this embodiment, measurement of a subject's scaled scalp distributions will differ in lying versus truth telling conditions, thereby providing an index of deception. This procedure differs from the prior methods of looking at P300 amplitudes which were unscaled.

There are many ways to scale. One way is taught by McCarthy and Wood (See, McCarthy, G. & Wood, C. C., Scalp distributions of event-related potentials: an ambiguity associated with analysis of variance models. *Electroencephalography and Clinical Neuropsycholgy*, 62, 203–208 (1985)). One way to scale the amplitudes is to convert the amplitudes into percentages within each condition. For example, suppose a task 1 yielded the values 2, 4, 2 microvolts at 3 sites in one condition (unscaled) and 12, 14, 12 microvolts in another condition, unscaled. These unscaled curves are clearly parallel. But if converted to percent, the first set of data becomes 50, 100, 50 (%), and the second set becomes about 86, 100, 86 (%). These scaled curves are clearly not parallel. The scaling method in the examples below is the one described by McCarthy and Wood as the vector length method.

When one looks at the significance of the interaction of condition by site in scaled amplitude in an analysis of variance (ANOVA), one is testing whether or not the curves are parallel. Because one has scaled out the main amplitude effects, the interaction which one examines is unconfounded by any such main effects which may exist. One is looking only at the shapes of the amplitude profiles, which have been made independent and orthogonal to the simple amplitude effect, which is the unscaled amplitude difference between tasks. This is the mathematical basis for an embodiment of the present method that distinguishes the previous methods, which looked at unscaled amplitude, usually at single sites.

Example of these novel embodiments are described in the examples below. In one example, the subject sees the phrase "Here is the sample", presented in blue color. Six seconds later, he sees on a screen a three digit number, in yellow color. This is the sample. Six seconds later he sees the first of 9 probes, each in white and 6 seconds apart. One probe is a perfect match, the others are all mismatches. Each subject sees about 20–25 of these 11-event cycles. There are two groups of subjects; one is the truth-teller group which gets all probes correct since this is an easy task. The other is the liar group which has been manipulated and motivated to be "wrong" about 50% of the time and at random. Note that in the liar group an individual can get an R (match) and respond either R or W, and likewise for a mismatch (W). So there are 4 ERP response types: RR, RW, WW, and WR. It has been shown that in liars there is a significant Truth/Lie by site interaction in scaled amplitudes, meaning that the RR and WW scaled amplitudes have a profile significantly different across sites (3 sites were used in the examples) than the RW and WR responses. One sees these effects within individuals.

This analysis cannot be used in field situations, because one may not be able to tell on which trials the subject will respond honestly, and which dishonestly. Every subject is a potential suspect. One needs in all subjects a set of P300 data based on known honest responses; i.e., one needs a control scalp distribution.

One approach is to use the P300 scalp distribution in response to the announcement (A) "Here is the sample" as the control distribution. There is no reason a priori, to expect that truth-tellers and liars will respond other than honestly to this stimulus; indeed they are not explicitly responding at all to this phrase, they just look at it, although the brain responds with a big P300 because it is a rare oddball. Thus, if further testing also confirms that the P300 scaled scalp distribution of a truth-teller in response to the announcement (A) is the same as that of a liar, then one can simply do within a subject a condition by site test on the A vs. the R scalp distributions. If it turns out that the honest A differs from the dishonest A, then one can correct the latter by subtracting (or adding) for each site the appropriate honest-dishonest A-difference from each A-value in the actually tested subject. Alternatively, one can simply give a different oddball task, prior to the investigatory task, during which no subject would lie, and use this preliminary task's scalp distribution to the oddball as the control distribution.

If instead of a matching to sample task, one were using a straightforward oddball paradigm (as in the earlier patents) with one item of guilty knowledge among several non-guilty items, then the control distribution could be the response to the "TBY" ("to be answered yes") item, "Taking lie test", or, just occasionally presenting the word "test." Or, as above, a preliminary oddball paradigm could be given on innocuous material which all subjects would be expected to handle honestly. An example, if one is testing subjects on recognition of their birth dates among others, the preliminary test could be presenting repeatedly a set of letters, with an occasional oddball number. The scalp distribution in response to the oddball number would be the control distribution with which one would compare the birth date profile. This preliminary paradigm (numbers vs. letters) could also be used with the match to sample paradigm.

It is emphasized that there are many potential paradigms for testing subjects, and each might require its own unique control (or preliminary) distribution.

In alternative embodiments, the analysis of the condition (control vs. test) by site interaction within subjects may be different. In addition, the number of sites may be different, as well as which sites are used. But the following general approach may used with any number of sites. One can use a bootstrapping method as in the previous patents, but applied to differences—between differences in condition—between sites:

Suppose it is determined that Fz, Cz, and Pz are the best set of sites to use, and one does not need any more sites than these. One has the set of c single C-sweeps (from the oddballs in the control condition, or trial-type C) at each of the 3 sites, and the set of t single T-sweeps (from the testing condition) at each of the 3 sites. (c and t are numbers of sweeps in the C- and T-sets, respectively.) These sweeps may have been pre-filtered to remove higher frequency noise. One goes into the C-set at site 1 and draws with replacement a set of c single sweeps and averages them. From the average, one computes P300 amplitude (P3/site 1/C) with either a base-peak or peak-peak method (as in U.S. Pat. No. 5,622,181). (These values are first scaled by dividing each by within condition constants. These are calculated as follows: using the vector-length scaling method, one sums the actual average Fz squared P300 with the squared average Cz and squared average Pz values, all for condition C, and takes the square root of the sum to yield the pythagorian vector length. The "actual average" values are the P300 values calculated by averaging all sweeps within a condition at one site.) One does the same for the T-set at site 1, yielding scaled P3/site 1 1/T. One does this iteratively (e.g. 100 times) to generate bootstrapped frequency distributions of P3 at each of the 3 sites for each of the 2 conditions. So one has 6 bootstrapped distributions of scaled P300 amplitudes. One now calculates the interaction term in the 2 by 3 ANOVA on the means of the bootstrapped conditions. If the number of sites used is more than 2, one should apply standard corrections for sphericity. The ANOVA will state what the probability is that the obtained interaction occurred by chance, and if this is less than 5 in 100, one assumes the interaction is significant at the 0.05 level, meaning that the T and C distributions are not parallel. (Different institutions may need to use different thresholds of significance.) The above method would apply to any number of sites.

With respect to the foregoing procedures, it is appreciated that there will probably be a difference between C and T distributions, even in truth-telling non-malingerers, because the stimuli that evoke the P300's are very different. Thus, it is required that a known truth-teller/normative distribution be obtained in the test paradigm, and then, that it be used to correct the simple (raw) C distribution from the control paradigm. One way to obtain this is to run about 100 non-suspect, normal subjects through both the simple control procedure (e.g., a simple oddball procedure). These subjects will have been told to do their best, and this can be verified from their behavioral response rates, i.e., with data from subjects scoring less than 98% correct removed. One can now determine (1) the average, scaled P300 amplitude distribution in subjects truthfully performing the test (T) procedure, as well as, (2) the distribution in these same subjects in response to the simple control (C) procedure. One can then determine the difference between these two distributions at each utilized site in the distribution function, i.e., scaled amplitude as a function of site. These differences can then be applied to each bootstrapped C-distribution iteration in future test subjects/suspects whose honesty is to be determined, prior to the ANOVA on (C vs. T) at each site to ascertain whether or not there is a (C vs. T) by site interaction in scaled data.

II. EXAMPLES

In the first of these examples, (Example 1), Truth-telling (Truth) and simulated malingering (Malinger) groups were tested in a matching-to-sample procedure in which each sample 3-digit number was followed by a series of nine test numbers, only one of which matched the sample. P300 was recorded during test-number presentation. Group analyses revealed differences between the P300's of the groups in unscaled amplitude but not latency, in response to match and mismatch stimuli. P300 amplitudes at Fz, Cz, and Pz were scaled to remove possible confounding effects of amplitude in tests of the interactions of site with other variables. Significant interactions of both stimulus-type (match vs. mismatch) and group (Truth vs. Malinger) with site were obtained. Within the Malinger group, a significant interaction was obtained (scaled data) between site and response type (honest vs. dishonest). These interactions suggest that deceptive and honest responding are associated with different sets of neural generators. In within-individual, bootstrap analyses, 100% of the Truth subjects and 87% of the Malinger subjects were found to have larger P300 responses at Pz to match stimuli than to mismatch stimuli on the basis of intra-individual bootstrap tests. This represents an improvement in comparison with the related, previous report on matching-to-sample test using only one test stimulus per sample.

The second and third of these examples describe experiments using a P300-enhanced Forced Choice Procedure to investigate simulated amnesia in a matching-to-sample task. In Example 2, successful manipulation of subjects towards different behavioral hit rates (75–80% vs. 85–90%) did not adversely affect the diagnostic sensitivity of match-mismatch Pz-P300 amplitude analyses, allowing detection of 69% of simulators. Pz-P300 amplitudes of simulators (Malinger group) were as large as those of truth-tellers (Truth group, a control), indicating no dual task-related (malingering) reduction across different behavioral hit rates. Example 3 found no main effect of oddball type, match vs. mismatch, on P300 (P3) amplitude with a mismatch-rare variant of the P3FCP. This study also revealed larger Pz-P3's in the malingering (vs. truth-telling) condition. Subsequent topographical analyses suggested different Truth and Malinger scaled P3 scalp amplitude topographies in both these sets of P3FCP data and in those from a previous autobiographical memory paradigm. Further analysis yielded preliminary evidence for a common deception-related P3 amplitude topography across different paradigms/conditions.

The possibility of similarly distinct Truth and Malinger topographies in another memory task was examined. In a previous study which used a task involving autobiographical information (a subject's birthday was utilized as oddball stimulus), P3 (at Pz only) was successfully detected in response to oddballs in subjects instructed to simulate malingered amnesia (See, Ellwanger, J., Rosenfeld, J. P., Sweet, J., & Bhatt, M. Detecting simulated amnesia for autobiographical and recently learned information using the P300 event-related potential. *International Journal of Psychophysiology*, 23, 9–23. (1996)). This previous study did not include task by site analysis, however that analysis is reported here. As in the P3FCP paradigm in the previous study, all Triarchic Model (See, Johnson, *Triarchic Model of P300 Amplitude, Psychophysiology,* 23(4), 367–384(1986)), variables were constant across conditions (Truth and Malinger), except for task complexity for the same reasons as given above. Thus, it was considered whether it might be possible, across paradigms, to characterize a deception-related profile based on these P3 scalp topographies. Both paradigms (P3FCP and Birthday) are different in terms of stimulus types and task requirements, with the only common factor between them being the task of malingering (in Malinger conditions). It might have been expected that dissimilar paradigms would produce both distinct paradigm—as well as condition—dependent scalp topographies.

Example 1

Subjects: 31 subjects were recruited from the department introductory psychology pool and were fulfilling a course requirement. All had normal or corrected vision.

Procedure: Following signing of consent form, instruction, and electrode attachment, subjects were seated in a recliner such that a video display screen was about 1 m from their eyes. They viewed a series of visual stimuli. The first, presented in yellow, on a black background, announced "Here is the sample" and was on for 2 seconds. Six seconds after onset of this announcement, a 3-digit number, the sample number, was presented in blue color for 2 seconds. One half second after the sample was cleared, the message "Respond" appeared, which instructed the subject to repeat the sample aloud. This message remained on for 2.5 seconds, after which, the time for responding expired as the "respond" message was cleared. After it was cleared, a 1 second delay interval (of no stimulus or response) intervened prior to the start of the next trial. Six seconds after the sample presentation, EEG recording began for 2.048 seconds. The first of nine test numbers, presented in white, appeared 104 ms after recording onset and remained on until the 2.048 second epoch expired. A half second later, the "respond" message appeared. The subject was required to repeat the number, followed by a left button press for "no" (not a match) or a right press for "yes" (a match). The response, again, was to be made in 2.5 seconds. Another 1 second delay preceded the start of the next test trial. Note that all visual stimuli (announcement, sample, test) were presented every 6 seconds. There were eight more test stimuli presented as described, followed by the second cycle of announcement, sample, and 9 test trials. In each cycle, there was one perfect match which could appear randomly, in any one of the second through ninth test positions. Mismatches, containing no digits in common with samples, appeared on other test trials, match probability was thus= 0.111. These cycles were presented until 256 artifact-free test trials were collected. (Rare trials on which the subject forgot to press a response button within the 2.5 second response window were not rejected although these were not analyzed, see Table 1 and results).

Subjects were randomly assigned to two groups. In the Truth group, they were instructed to do their best, and to wait for "respond" instructions before pressing a button or repeating a sample. In the Malinger group, subjects were also asked to simulate cognitive deficit by pretending "that you have memory deficit due to an injury. In other words, don't get all of the responses right. So, sometimes when you know that the number matches the sample, press the button on the left and say 'no' making believe that you think they don't match. In the same way, sometimes when you know the number does not match the sample, press the button on your right and say 'yes', as if they did match. On average, people with real brain damage don't do perfectly, but they get about half of them right, and they make mistakes on matches as well as mismatches. Their pattern of errors is random, not systematic. Because only one match appears in each series of white test numbers, you will have many more chances to say yes to a mismatch than to say no to the match." The Malinger subjects were told that if both their brain waves and behaviors "beat the test," they would be mailed $10 after the end of the quarter.

EEG recording and Analysis: EEG was recorded with Grass P511k preamplifiers with gain=100,000, and filters set to pass signals between 0.1 and 30 Hz (3 db points). Electrodes (Ag—AgCl) were attached to Fz, Cz, and Pz referenced to linked mastoids with the forehead grounded. EOG was recorded from a bipolar pair of electrodes above and below the eye. EOG signals>80 $\mu$V led to trial rejection and replacement. Amplified signals were led to 12-bit A/D converters (Keithley-Metrabyte) sampling at 125 Hz, and the digitized signals led to a 386–40 mHz PC for on-line sorting, averaging, and storage. A computer program also controlled stimulus presentation, and performed off-line filtering and analyses.

P300 amplitude can be determined in at least two ways. In a first way, a baseline-to-speak method, the maximally positive 104 ms (13 data points) segment from 400 to 1000 ms post-stimulus is found, and the average of the 104 ms of EEG preceding the stimulus is subtracted from it. The midpoint of this maximum segment is defined as P300 latency. In the second method, instead of referencing P300 amplitude to the pre-stimulus baseline, the positive maximum is referenced to the subsequent maximum negative segment of 104 ms occurring in the interval between P300 latency to 1600 ms post-stimulus. This peak-to-peak amplitude is defined as the difference between positive and negative peaks. In several previous studies, it has been consistently found that the peak-to-peak method yields on average 20% superior detection rates in guilty or malingering subjects in individual tests. It also has yielded results in group ANOVAs which are virtually identical to results with the baseline-to-peak method. Therefore, it was decided a priori to present results here based solely on peak-to-peak determinations for both individual and group analyses.

For group analyses, P300 latency and amplitude were based on unfiltered averages for each subject. For individual analyses and for display (FIG. 1), single sweeps and averages were digitally filtered to pass low frequencies; 3 db point: 4.23 Hz. For task-by-site interactions, average P300 amplitudes within each subject were filtered using the vector length method (See, McCarthy, G. & Wood, C. C., Scalp distributions of event-related potentials: an ambiguity associated with analysis of variance models. *Electroencephalography and Clinical Neuropsychology*, 62, 203–208 (1985)). Within each group and/or stimulus/response condition, the average Fz, Cz, and Pz values for the condition/group were squared, and the square root of the sum of the squared values was used as a denominator by which individual Fz, Cz, or Pz values within the condition/group were divided.

As shown in Table 1 and discussed in Results, within both the Truth and Malinger groups, the two stimulus conditions were match (R for "right") and mismatch (W for "wrong").

TABLE 1

BEHAVIORAL RESULTS

| Stimulus | Response | Res. Outcome/ Code | Truth Group | | Malinger Group | |
|---|---|---|---|---|---|---|
| | | | Expected Proportion | Actual Proportion | Expected Proportion | Actual Proportion |
| Match(R) | Match(R) | RR | 1.0 | .91 | .5 | .52 |
| Match(R) | Mismatch (W) | RW | 0.0 | .09 | .5 | .48 |
| Mismatch (W) | Mismatch (W) | WW | 1.0 | .998 | >0 | .94 |
| Mismatch (W) | Match(R) | WR | 0.0 | .002 | >0 | .06 |

Note:
These are proportions of total within stimulus category, i.e., R = RW + RR, W = WW + WR.

In the Truth group, most trials involved correct and honest responses so that the stimulus/response conditions for this group were Match-True (RR) and Mismatch-True (WW). In the Malinger group, there were the two additional categories involving deceptive responses, Match-Lie (RW) and Mismatch-Lie (WR).

For individual diagnosis, only the Pz amplitude was focused upon, as a comparison of hit rates of present and previous paradigms for detection of simulated deficit in matching-to-sample tasks was of concern, and the previous studies utilized P300 amplitude at Pz only. In the present study, bootstrap methods were utilized for individual analysis. The bootstrap test was utilized here to decide within each subject whether or not the P300 amplitude was greater in response to match (R) than to a mismatch (W). More specifically, the inquiry was whether the probability was more than 95 in 100 that the difference between the average match P3 and mismatch P3 is>0. For each subject, however, there was available only one average match P3 and one average mismatch P3. Answering the statistical question required distributions of average P3 waves, and these actual distributions were not available. However, it was possible to bootstrap the distributions, in the bootstrap variation used here, as follows:

After digitally filtering the single sweep set (matches and mismatches) for an individual, as described above, a computer program went through the match set and drew at random but with replacement a set of $n_1$ waveforms. It averaged these and calculated P3 from this single average using the maximum segment selection method described above. Then a set of $n_2$ waveforms was drawn randomly with replacement from the mismatch set, and a mismatch average P3 was calculated. Bootstrapped means were based on the number $n_1=28$ for matches and $n_2=228$ for mismatches. (Note that 28=11% of 256 total trials. This was the programmed match frequency, and 228=256−28=the programmed mismatch frequency). The calculated mismatch mean P3 was subtracted from the comparable match value, and one thus obtained a difference value to place in a bootstrapped distribution contained 100 values after 100 iterations of the process just described. Iterations yielded differing (variable) means and mean differences due to the sampling-with-replacement process. In order to state with 95% confidence that match and mismatch were indeed different, it was required that the value of zero difference not be within±1.96 standard deviations from the mean of the bootstrapped distribution. The validity of Bootstrapping rests on the ability of the bootstrapped distribution to allow a good estimation of the population variance of the average P3 value, when only one sample average of several single sweeps is available for a given subject. (One could also utilize independent t-tests within-subjects, as done previously. It has been found this traditional approach is less sensitive, probably related to its dependence on noisier values based on single sweeps.)

Results (Behavioral)

Of the 256 trials per subject, 11% (28) were programmed to be match (R) trials, with the remaining 89% (228) mismatch trials. In the Truth group, in fact 11% and 89% were closely approximated by the actually obtained mean numbers of R trials (=25.1) and W trials (202.6). (These sum to about 228 which is 28 trials short of 256. The 28 missing trials were trials in which the behavioral response was either absent or late. A similar discrepancy was seen in the Malinger group.) In the Malinger group, the expected 11% and 89% respective R and W probabilities also closely approximated by the actual mean number of Rs=28.9 and Ws=217.6. Table 1 shows the expected and obtained numbers of match and mismatch responses associated with R and W stimuli. It appears that expectations were largely met with the exception that the Malinger subjects mostly responded honestly on the W trials. A 50—50 split would have been preferred for W's, as was obtained for R's, nevertheless, this still yielded about 13–15 sweeps per WR average.

ERP: Group Data, Qualitative Observations

Figure 1A:
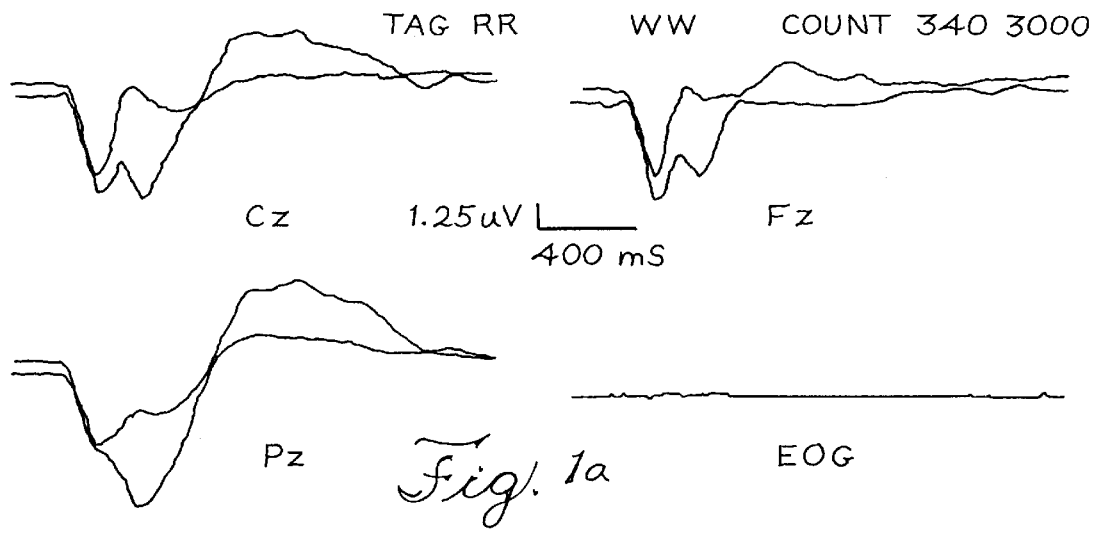
FIG. 1a shows a series of superimposed, grand-averaged, filtered (3 db at 4.23 Hz) ERP waveforms associated with RR (darker) and WW (lighter) trials in the Truth group. "Count" refers to the number of sweeps in each respective average.
Figure 1B:
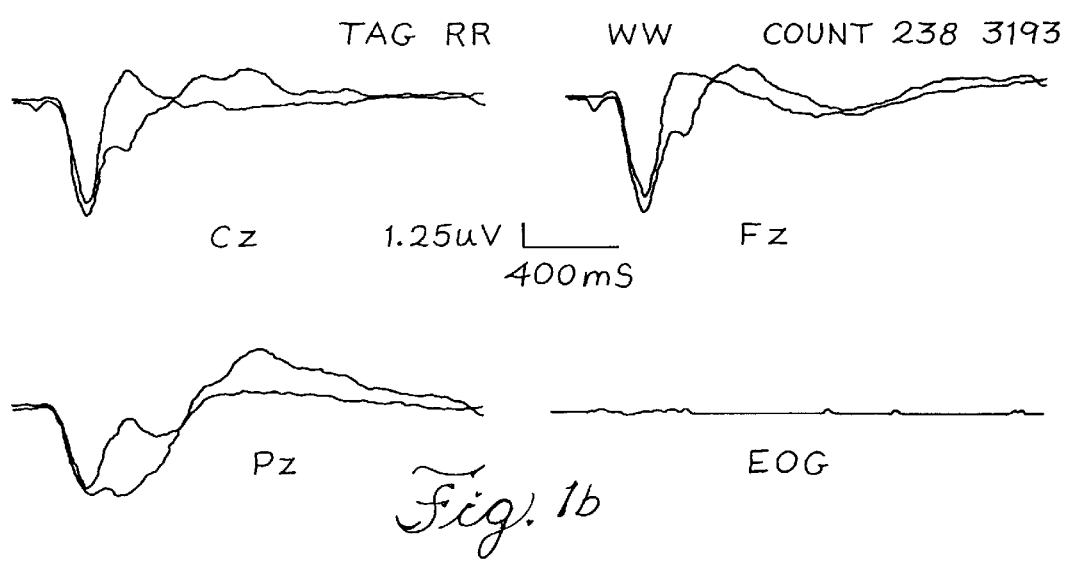
FIG. 1b is similar to FIG. 1a, but for the Malinger group.
Figure 1C:
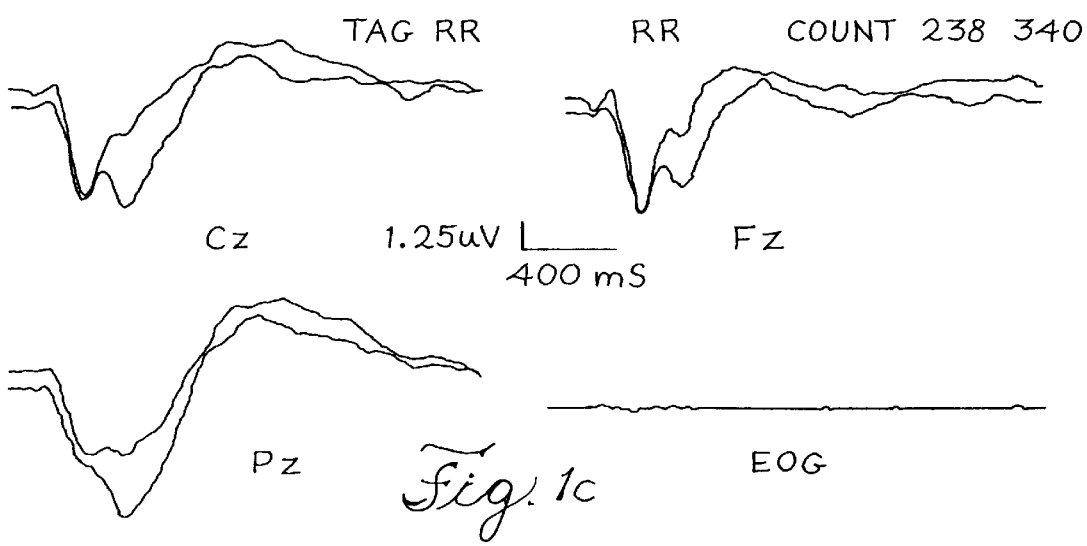
FIG. 1c is similar to FIG. 1a, except RR sweeps are superimposed for Truth (lighter, larger), and Malinger (darker, smaller) groups.
Figure 1D:
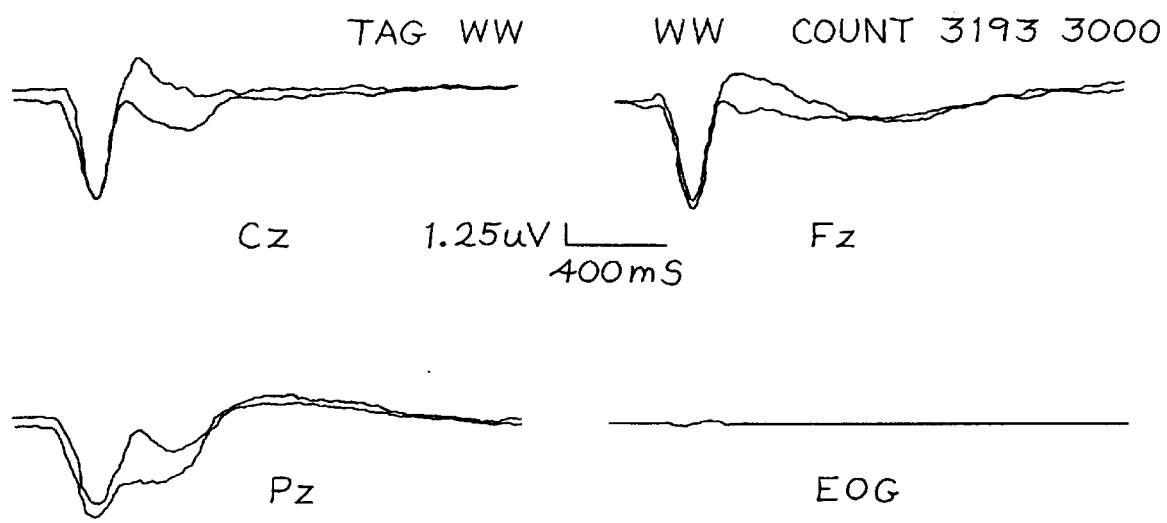
FIG. 1d is similar to FIG. 1c, except WW waveforms are superimposed.
Figure 1E:
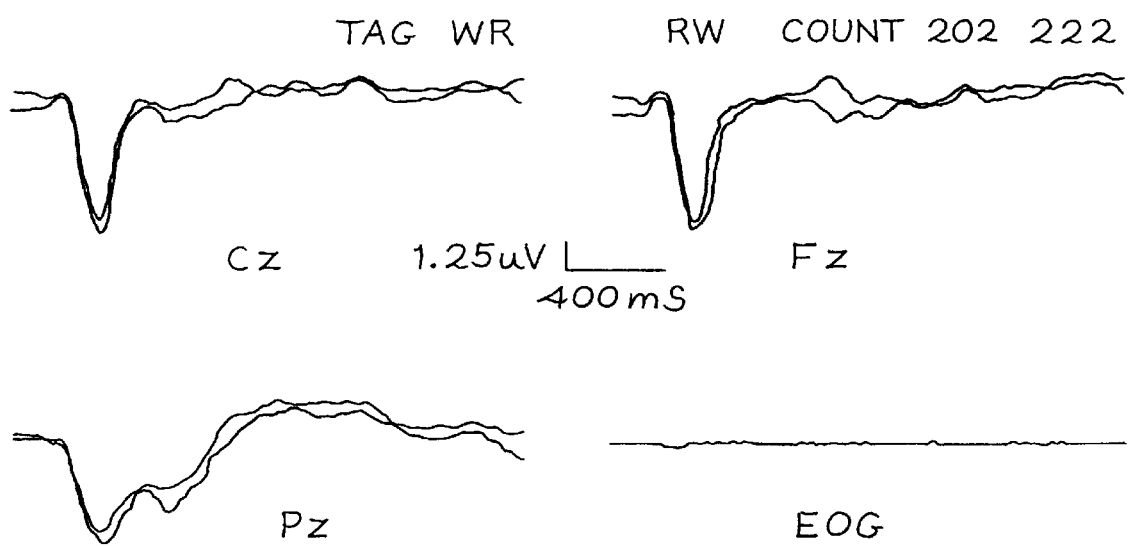
FIG. 1e shows ERPs in the Malinger group associated with dishonest responses to match (RW) and mismatch (WR) stimuli. WW represents a mismatch response to a mismatch stimulus.

FIGS. 1A–1E show representative grand average waveforms based on filtered individual averages from which higher frequencies were blocked (3 db point at 4.23 Hz). The superimposed RR and WW waves for the Truth group are in FIG. 1A. (Since over 90% of the R responses in the Truth group were RR, the superimposed R and RR waveforms, not shown, are nearly identical.) It appears (FIG. 1A) that the rare RR P300's are larger and earlier than the frequent WWs. It also appears that P300 is largest at Pz and smallest at Fz, as is ordinarily expected. In the Malinger group (FIG. 1B), the same trends in RR vs. WW are seen, although the Malinger P300s are smaller overall than the Truth waveforms. This is apparent in FIG. 1C where the RR waveforms for both groups are superimposed, and in FIG. 1D where WW waveforms are superimposed. FIG. 1E shows the deception-associated responses, RW and WR, from the Malingering group, and strongly suggests that the deception condition removes much if not all of the difference between P300 responses seen in truth-telling to the 2 differing kinds of stimuli.

ERP: Group Data, Unscaled Amplitude Analysis

Figure 2:
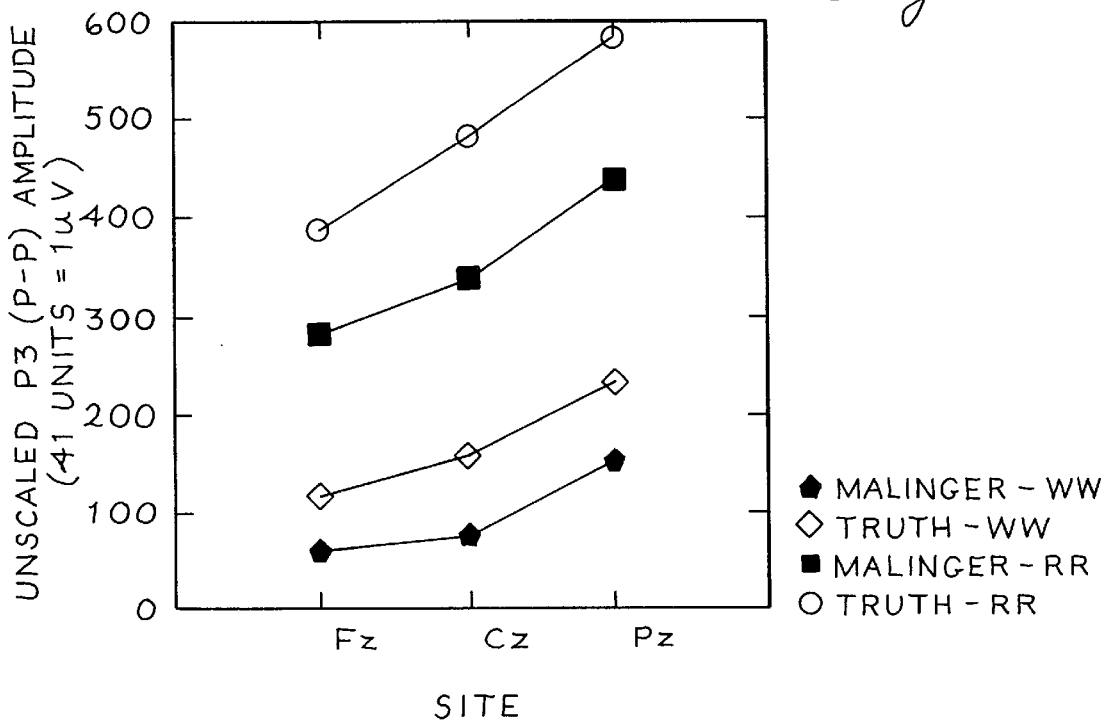
FIG. 2 is a diagram plotting unscaled, computer-determined P300 amplitudes as functions of site, group (Truth or Malinger), and stimulus, with all honest responses. RR represents a match response to a match stimulus. WW represents a mismatch response to a mismatch stimulus.

FIG. 2 displays the computer-determined, mean P300 amplitudes as a function of site for Truth and Malinger groups responding honestly (and correctly) to match and mismatch stimuli. The data of FIG. 2 (involving RR and WW responses) were submitted to a 3-way ANOVA, group Truth vs. Malinger) being the one between-subjects independent variable. The within-subjects variables were site (Fz vs. Cz vs. Pz) and stimulus type, (Match/RR vs. Mismatch/WW). In all subsequent results "pg" refers to Greenhouse-Geisser-corrected probability. When this correction for sphericity is not necessary, the familiar "p" is reported. Confirming the visual impression of FIG. 2, there was a main effect of group (Truth vs. Malinger), $F_{1,29}=9.77$, p<0.005. There were also main effects of stimulus type, $F_1,29=173.78$, pg<0.001, and site, $F_{2,58}=70.45$, p<0.001. only significant interaction was that of stimulus type by site, $F_2,58=8.67$, pg<0.004. This is reflected in the figure by steeper match curves than mismatch curves as a function of site.

A plot similar to FIG. 2, but for all match (R=RW and RW) and mismatch (W=WW and WR) P300s is not shown, but is similar to FIG. 2, particularly for the Truth group, as expected. A three way ANOVA on these (R and W) data revealed significant main effects of group, $F_{1,29}=12.56$, p<0.002; stimulus type, $F_{1,29}=143.26$, p<0.001; and site, $F_{2,58}=65.59$, pg<0.001. It will recalled that data for the Truth group was virtually identical for both of the forgoing ANOVAs, since over 90% of the R responses are RR responses in the Truth group; such is not the case for the Malinger group.

Figure 3:
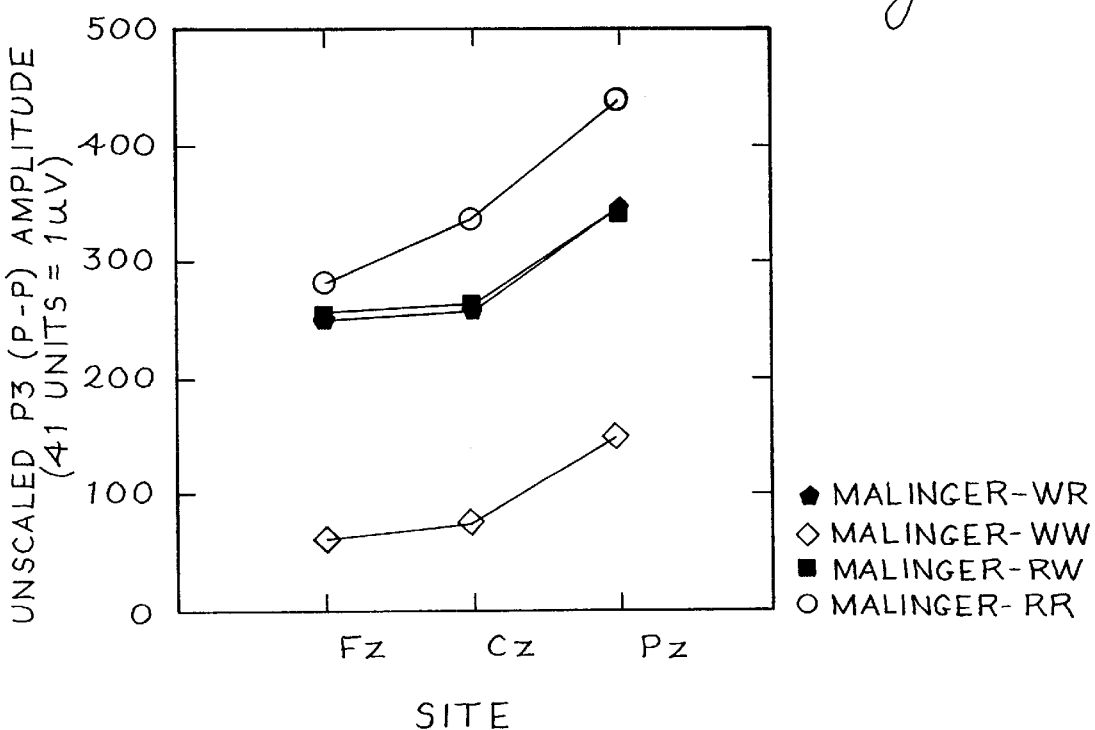
FIG. 3 is a diagram plotting unscaled, computer-determined P300 amplitudes as function of site and stimulus-response combination within Malinger group only. RR, WW are honest responses as in FIG. 2. RW represents a match response (lie) to a mismatch stimulus.

FIG. 3 is a plot of computer-determined, mean P300 amplitudes as a function of site within the Malinger group only. There are four types of separately averaged P300 amplitudes plotted, 1) Match stimuli to which subjects responded truthfully. (RR) and 2) deceptively (RW), 3) Mismatch stimuli to which subjects responded truthfully (WW) and 4) deceptively (WR). FIG. 3 suggests profound differences due to stimulus type during honest responding, but remarkably, no difference during deceptive responding. A 3-way, repeated measures ANOVA was performed on these data, with the three within-subject variables being site, stimulus type, and response type (honest vs. deceptive). There was a main effect of stimulus type, $F_{1,15}=37.15$, p<0.001, which was clearly carried by the honest responses as confirmed by the interaction of stimulus and response type, $F_{1,15}=28.55$, p<0.001. There were also main effects of response type, $F_{1,15}=17.52$, p<0.002, and site, $F_{230}=33.73$, pg<0.001. Additionally, there was an interaction of response type (honest vs. deceptive) and site, $F_{2,30}=3.34$, pg<0.052.

ERP: Group Data; Latencies

Table 2 shows the P300 grand average peak latencies, sorted by group and response type.

TABLE 2

| | LATENCIES (in msec) | | | | | | | |
|---|---|---|---|---|---|---|---|---|
| | Truth Group | | | | Malinger Group | | | |
| Outcome Code | RR | WW | RW | WR | RR | WW | RW | WR |
| Fz | 467 | 521 | — | — | 477 | 587 | 481 | 528 |
| Cz | 461 | 530 | — | — | 476 | 588 | 514 | 536 |
| Pz | 458 | 483 | — | — | 476 | 507 | 498 | 503 |

Note:
SD range: 61–172 msec.

(RW and WR data in the Truth group are shown in view of the rare or absent RW and WR responses in this group.) The SD range of the means in Table 2 varied from 61–172 ms. The only apparent qualitative observation apparent in the table is that match stimuli elicit faster responses than do mismatch stimuli. A 3-way ANOVA on the P300 latencies of truthfully answered trials was performed; the between-group variable was group (Truth vs. Malinger), and the within-group variables were site and stimulus type (RR vs. WW). In contrast to results with amplitude, group had no effect on latency ($F_{1,29}=0.96$, p>0.33). There were, however, effects of stimulus type ($F_{1,29}=24.4$, p<0.001) and site ($F_{2,58}$, pg<0.01). There was only one other significant effect, an interaction of stimulus type by site, $F_{2,58}=7.61$, pg<0.003.

A similar 3-way ANOVA on latencies associated with honest and dishonest responses combined (i.e., RR and RW=R vs. WW and WR=W) yielded similar results, most importantly, no effect of group (Malinger vs. Truth), $F_{1,29}=0.87$, p>0.35. There were effects of stimulus type ($F_{1,29}=19.9$, p<0.001) and site ($F_{2,58}=8.49$, pg<0.003), as well as an interaction of stimulus type and site, $F_{2,58}=7.23$, pg<0.005. No other significant effects were obtained.

A 3-way ANOVA was also performed on latencies within the Malinger group, only. In this repeated-measures ANOVA, the independent variables were stimulus-type, response-type, and site. Consistent with the failure to find group differences in latency described above, the present ANOVA found no effect of response type ($F_{1,15}=0.39$, p>0.54). However, there were significant effects of stimulus type ($F_{1,15}=13.63$, p<0.003) and site ($F_{2,30}=5.27$, pg<0.012). There were also significant interactions of stimulus and response types ($F_1$, 15=5.02, p<0.042), and of stimulus type and site ($F_2,30=8.48$, pg<0.006). The triple interaction approached significance, $F_{2,30}=2.85$, pg<0.09.

ERP: Group Data; Scaled Amplitude Analysis

In the analyses of these scaled data, only interactions were considered, since, as pointed out (See, McCarthy & Wood, above), condition and group effects are obviated intentionally by the scaling procedures. Moreover, only the interactions speak to the issue of condition-specific neurogenerators.

Figure 4:
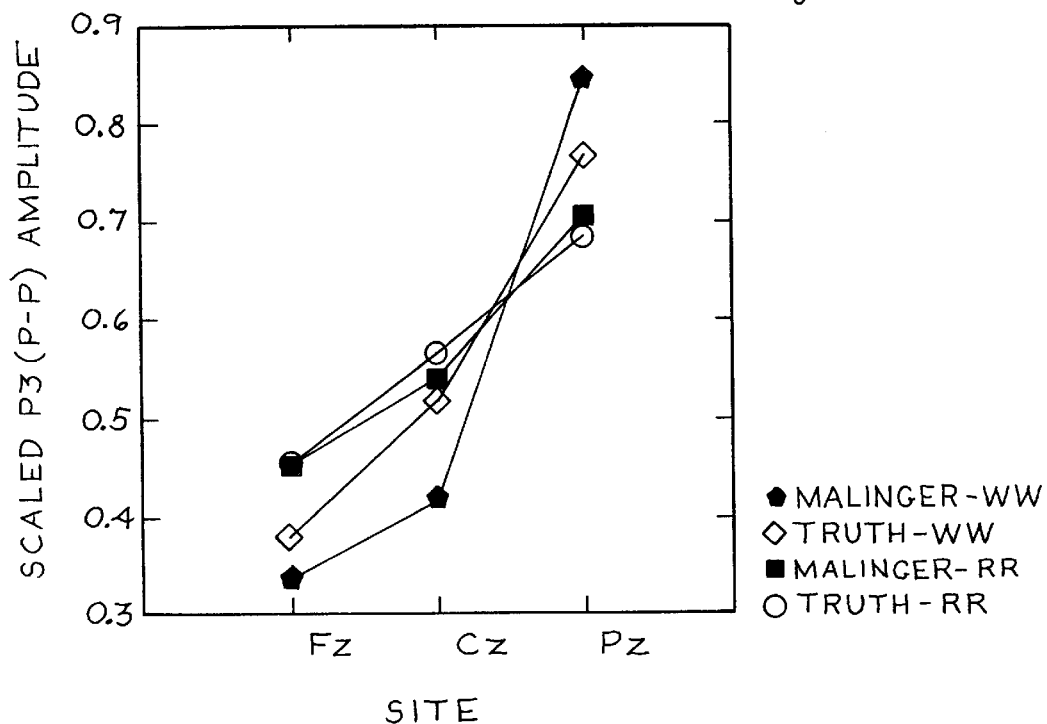
FIG. 4 is a diagram similar to FIG. 2, but for scaled amplitudes.
Figure 5:
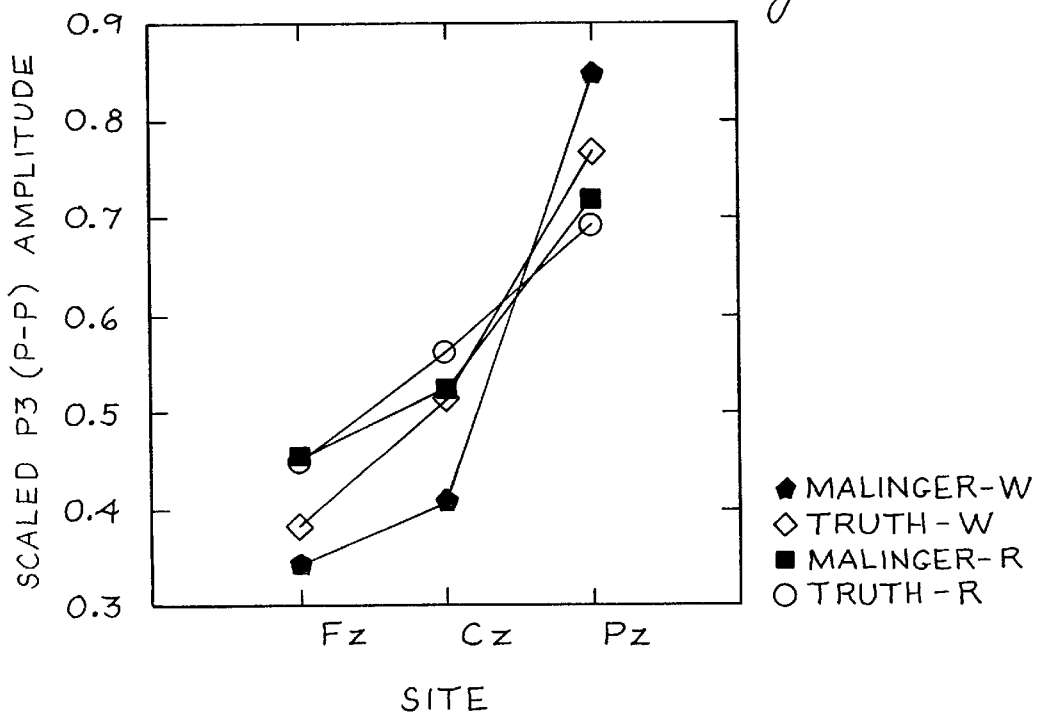
FIG. 5 is a diagram plotting scaled, computer-determined P300 amplitude as a function of site, group, and stimulus type, regardless of response; R=match, W=mismatch.

FIG. 4 is a plot of mean, vector-length-scaled P300 amplitude as a function of the within-group variables, site and stimulus-type, and of the between-group variable, group. It is the scaled equivalent to FIG. 2 and thus also shows only honestly responded-to responses. FIG. 5 is similar, except that it shows scaled amplitudes for all responses to match combined (RW+RR=R), and for all responses to mismatch combined (WR+WW=W). These figures are similar and suggest that the truth-telling group shows fairly linear functions of scaled amplitude across site, whereas the deceptive (Malinger) group shows more quadratic-looking functions. The data of FIG. 4 were submitted to a 3-way ANOVA (group×site×stimulus type; all within-subjects). The overall ANOVA revealed a significant interaction of stimulus type and site ($F_{2,58}=9.01$, $p<0.003$). The interactions of conditions with other variables, including the triple interaction, were not significant ($p>0.2$). Looking, however, at the single df polynomial contrasts, both quadratic polynomial interactions of site-by-group, and of site-by-stimulus type reached Bonferronni-corrected significance levels. (The correction was used since the tests were post-hoc. Since based on FIG. 4, only the 2 interactions just noted were considered, the alpha level was corrected from 0.05 to 0.005/2=0.025.) The interaction in quadratic order of group by site yielded $F_{1,29}=5.78$, $p<0.002$. The interaction (in the quadratic term) of group and site, the effect of major interest here, reflects the impression of FIG. 4 that the Malinger group shows a quadratic component in the functions relating scaled amplitude to site, whereas the Truth group does not clearly show this trend.

The data of FIG. 5 revealed similar effects in a similar 3-way ANOVA: In the main analysis, only the stimulus type×site interaction was significant, with $F_{2,58}=8.66$, $pg<0.002$; i.e., none of the other interactions with group reached significance in the main analysis. The quadratic component of the stimulus type×site interaction was also significant (with respect to corrected alpha=0.025) in a single df polynomial contrast: $F_{1,29}=15.6$, $p>0.00$ 1. So, also, was the group by site quadratic component significant; $F_{1,29}=6.79$, $p<0.015$.

It is noted that the data for FIG. 4 involve completely comparable stimulus types and (honest) response types between groups, yet the Malinger group does not resemble the Truth group in scaled scalp distribution. This suggests that the deceptive state lasts longer than the deceptive behavioral response, and appears to carry over into subsequent trials involving honest responses.

Figure 6:
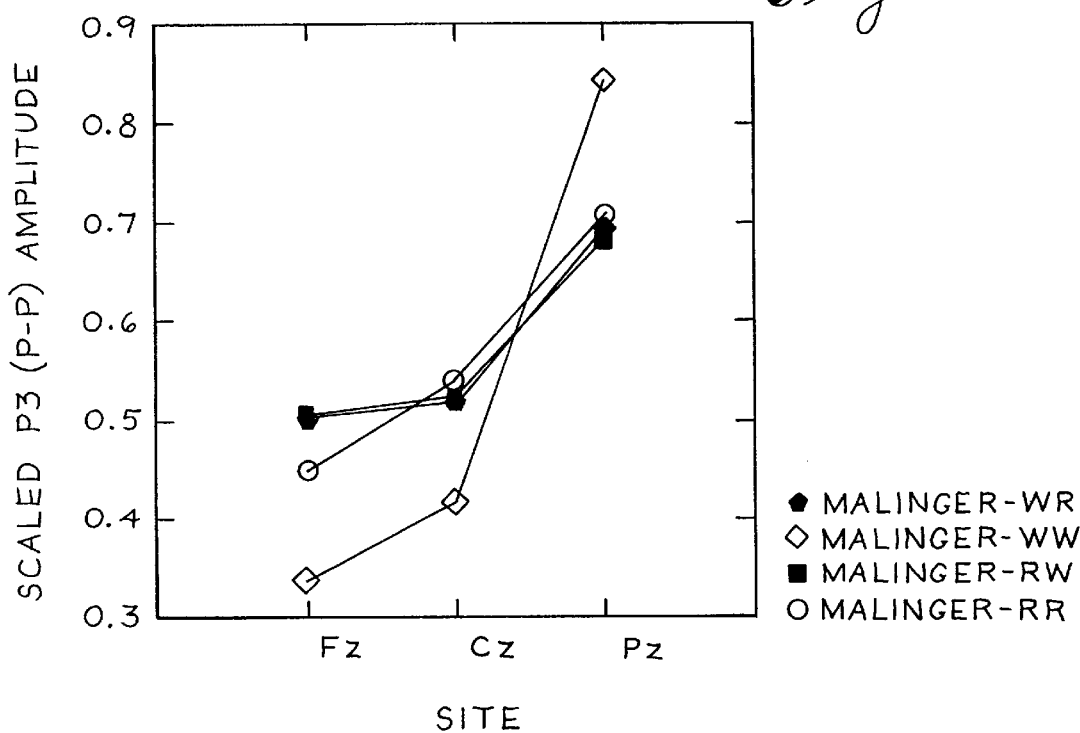
FIG. 6 is similar to FIG. 3, but scaled amplitudes.

FIG. 6 is the scaled amplitude equivalent of FIG. 3 and shows scalp distributions within only the Malinger group for honest and deceptive responses to both matches and mismatches. As in FIG. 3, the deceptive response distributions for both match and mismatch stimuli seem virtually superimposed, whereas there appears to be a clear interaction of site and stimulus type for the stimuli which were responded to honestly. These data were submitted to a completely within-subject, 3-way ANOVA involving site, stimulus type, and response type. The significant interactions were (most importantly) of response-type. The significant interactions were (most importantly) of response-type (honest vs. deceptive) and site ($F_{2,30}=13.3$, $pg<0.001$), and also the 3-way interaction ($F_{2,30}=4.4$, $pg<0.03$). The other interactions yielded $p>0.1$.

ERP Individual Data: Within-Individual Scalp Profile Analysis

Figure 7:
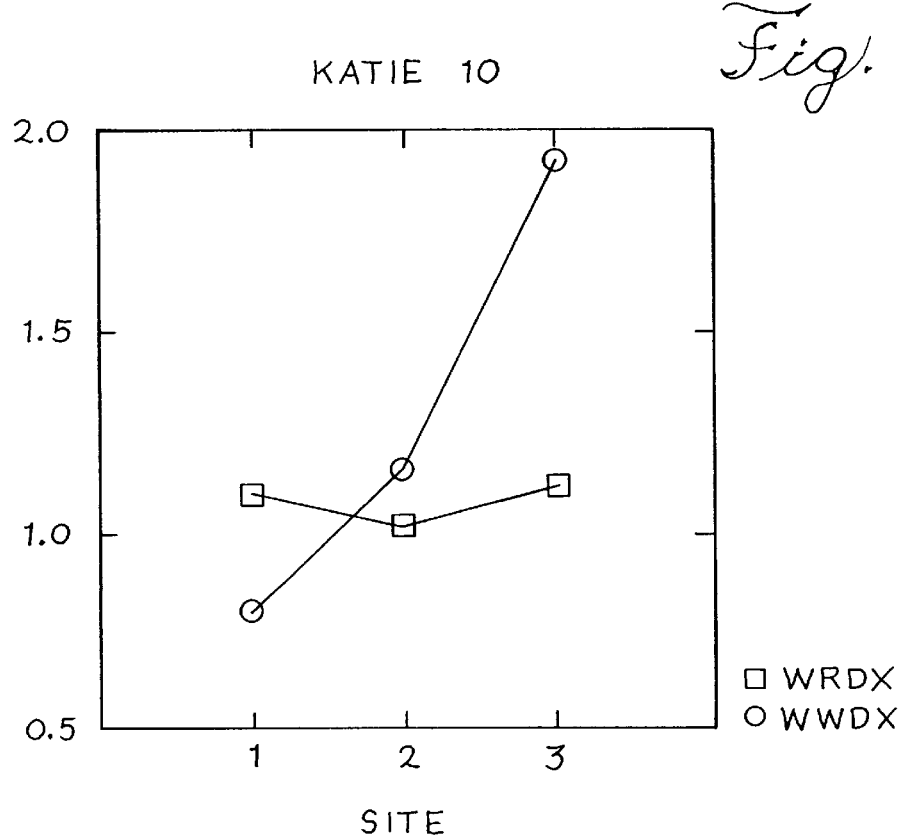
FIG. 7 is a diagram showing the scalp distributions for mismatch responses honestly responded to and mismatch responses within one individual.

FIG. 7 shows within one subject (from the study just described) the scaled scalp distributions for mismatch responses honestly responded to (WW) and mismatch responses to which this subject lied (WR). Sites 1, 2, and 3 are Fz, Cz, and Pz, respectively. The non-similarity of the two profiles is clear. Bootstrapped distributions for the two profiles were obtained, and analysis of variance with the bootstrapped data revealed, within this subject, a significant condition (truthful versus deceptive response) by site interaction. This kind of analysis has now been done on 5 experimentally malingering individuals from this study with the same result. This testifies to the feasibility of using the profile analysis on an individual basis for real world diagnostic use.

Discussion

The most striking dual finding here was that shown in FIG. 3 and especially FIG. 6. The latter shows 2 effects: 1) In the Malingering group, honest responding is associated with scaled P300 amplitude distributions which vary according to stimulus type, suggesting that the two different kinds of stimuli used here, match and mismatch, activate differing subsets of stimulus-specific neurogenerators. Of course, the generators are likely representing not simply specific stimulus attributes, but, more importantly, the differing psychological processes engaged by the differing stimuli. 2) Deceptive responding, in contrast, produces scalp distributions which appear not to differ as a function of stimulus type, and which virtually superimpose. One might have anticipated that both stimulus type (R vs W) and response type (honest vs deceptive) might influence scalp distributions such that both the response×site and stimulus×site interactions would be significant. In fact the former, but not the latter interaction was significant, thus partially accounting for the also significant 3-way interaction. The result implies that the subject's self-awareness of his/her deceptive action becomes the dominant psychological process during a time period involving only some deceptive responses, such that the match-mismatch difference in the stimulus presented loses influence.

Only three midline electrodes were used here, and it is possible that during deception periods, stimulus effects may be seen at other sites. If this is so, however, there is an important implication: It is that in deception, a set of neurogenerators are activated which, though in other conditions may reveal various effects (e.g., of stimulus type), they appear to specialize in deception representation when deception occurs. This is not necessarily to say that there are a set of neurogenerators in the brain which intrinsically respond to the act of telling lies in the same way that edge detectors in visual cortex respond to borders. Such a claim would suggest the existence of the elusive "specific lie response." It is more possible instead that this set of neurogenerators represents activation of a more or less unique set of neurons which are activated by the various cognitive and emotional subcomponents of deception. Subsets of this "deception set" can then be separately activatable via other (non-deceptive) mechanisms. Activation of what is loosely called the deception set, may be the substrate of an individual's self-awareness of deception.

This is consistent with the group comparison data of FIGS. 4 and 5. The scaled data of FIG. 4, representing trials in which honest responses were given to matches and mismatches by both Truth and Malinger subjects, did show a stimulus type-by-site interaction. In FIG. 5, representing all trials (honest and deceptive), the same interaction is obtained. The fact that about half the match trials in the Malinger group were dishonestly responded to (but averaged together with honestly responded to matches) does not prevent the stimulus type-by-site interaction. This might seem inconsistent with the data of FIG. 6, discussed above as indicating that deceptive responding swamps the stimulus type-by-site interaction, however, two facts explain the apparent inconsistency: 1) The data of FIG. 6 involve comparisons all within the Malinger group, whereas the data of FIG. 4 involve group comparisons. As will be discussed below, group membership may well have its own effects which compete with those of response type. 2) Regarding FIG. 5, it is noted that the match averages include responses to both honestly and dishonestly responded to match stimuli in the Malinger group. The putative deceptive response swamping effect in this data set may be additionally diluted by the truthful responses in the match averages.

The key findings in FIGS. 4 and 5 were that the graphs of scaled amplitude as functions of site were quadratic in the Malinger group but not the Truth group. These findings were post-hoc. The implication, especially in FIG. 4, where responses are truthful in the Malinger group, is that being in an ongoing psychological state of self-awareness that one is responding dishonestly (half the time) appears to activate a particular neurogenerator set even during truth-telling trials; i.e., effects of self-awareness of deception can carry over into intervening moments of honest responding. Actually, the trial structure used here also implies that self-awareness of deceptive responding endures beyond and/or precedes the moment of responding, and is thus more of a tonic state than a phasic response. This implication is based on the fact that ERPs were recorded in immediate response to stimuli, however verbal responses (truthful or deceptive) did not occur until the recording epoch plus a delay period expired, 2.5 s (plus reaction time).

An implication of the present results is that a novel index is available for the field application of detection of deception. That is, it can be expected that a deception index based on scaled, or for that matter, unscaled scalp amplitude distribution of P300 can evolve. Scaled amplitude distribution shape or profile can provide information which is to some degree independent of what is provided by amplitude at one site alone. The addition of data from other sites may improve detection simply by increasing statistical power. But beyond this possible source of improvement, it is noted that with scaled amplitude distributions, the effects of simple amplitude are controlled across conditions, and one may compare distribution shapes as indices orthogonal to amplitude effects.

Example 2

Subjects: Subjects consisted of 25 undergraduates from the university psychology class pool, participating for credit in the introductory psychology course. All had normal or corrected vision, and were fully debriefed following their participation.

Procedures (General testing procedure): Subjects were seated in a recording room with a computer monitor. It was explained that when the test began, a three digit number would appear on the monitor, and each subject was instructed to repeat the number aloud as quickly as possible. The sample number remained on the screen for 3 seconds, after which it disappeared. Following a 3 second delay, a second number appeared in the same central screen location. This probe number either did or did not (in any digit) perfectly match the sample. The ERP was recorded from 104 msec prior to the probe onset to 1944 msec after its onset, resulting in a 2048 msec recording epoch. After the end of the epoch, a message "please repeat number" appeared on the screen below the probe. Subjects were instructed to repeat the probe at this time and then immediately say "yes" (for a match) or "no" (for a mismatch). An experimenter then recorded this response with a corresponding button press at the recording computer keyboard. The probe and repeat message were then cleared from the monitor and a new sample appeared after a 500 msec delay.

ERP Recording and Analysis

Silver-silver chloride electrodes were attached with conductive EEG paste to Fz, Cz, and Pz scalp sites. Linked mastoids served as the references with the forehead grounded. Electrodes were also placed supra- and sub-orbitally for EOG recording; i.e., eye movement artifacts occurring during the recording epoch were detected and trials containing 80 $\mu$V or higher deflections were discarded and replaced. Signals were amplified 75,000 times by Grass p511-K preamplifiers with 3 dB filters set to pass signals between 0.3 and 30 Hz. Conditioned signals were led to an 8-bit analog/digital converter sampling one point every 8 msec, and then to a microcomputer for on-line analysis and data storage.

P3 Analysis

Two methods of measuring P3 amplitude were utilized. In one method, a computer program calculated the value of each 104 msec segment (13 data points) of waveform in the interval from 472 to 1200 msec. The maximum positive segment was then subtracted from the average value of the pre-stimulus baseline (of the 13 points of sampled EEG preceding probe stimulus onset). This value was the baseline-to-peak (b-p) value. The time measured from stimulus onset to the midpoint of the maximum segment was taken as the P3 latency. In the peak-to-peak (p-p) method, the computer program found the maximum positive segment from 472 to 1200 msec as in the b-p method, but subtracted it from the subsequent maximum negative segment, which it finds by determining the maximum negative 104 msec segment in the interval from the previously found P3 latency to the end of the sweep. In detection of concealed information, the p-p measure was diagnostically superior to the b-p measure. While both measures were used in this example to evaluate P3 effects, it was anticipated that the p-p measure would yield the best outcomes.

Example 3

Subjects

Subjects were 10 undergraduates in an advanced psychophysiology lab course. All were well-informed about the aims and results of the studies, as well as the procedures and methods of the Hiscock Forced Choice Procedure. All subjects had normal or corrected vision.

Procedures (General testing procedure): The P3FCP was administered to subjects in the same manner as in Example 2. One difference in instruction (described below) occurred during Malinger blocks.

ERP Recording and Analysis

All recording procedures were identical to those in Example 2.

Scalp Amplitude Distribution Analysis: Example 3

Statistical analysis of the ERP data from Example 3 was done to assess the possibility that these tasks (i.e., simulated malingering and truth-telling) may elicit ERPs with differing amplitude distributions across the scalp. In his *Triarchic Model of P300 Amplitude, Psychophysiology*, 23(4),. 367–384(1986), Johnson postulated that a difference in scalp amplitude distribution across tasks suggests that these different tasks involve differentially localized neural generators in the brain. This would be illustrated by a task by site interaction in an ANOVA. In order to perform an unambiguous analysis however, ERP data should first be scaled so as to ensure that the comparisons are confined to scalp topography differences alone and not to effects of overall amplitude differences between tasks (See, Johnson, R., Miltner, W., & Braun, C., "Auditory and somatosensory event-related potentials I: effects of attention," *Journal of Psychophysiology*, 5, 11–25). Three scaling methods were suggested by McCarthy, G. & Wood, C. C. in their "Scalp distributions of event-related potentials: an ambiguity associated with analysis of variance models," *Electroencephalography and Clinical Neuropsychology,* 62, 203–208 (1985), and their preferred vector length scaling method was used in the present analysis. This requires scaling all voltages (ERP amplitudes) at each site within a condition with its corresponding vector length calculated using within-condition scaling values. Task by site, within-subject ANOVAs of scaled data were then used to examine topographical differences. Both task (2 levels: Truth and Malinger and site (3 levels: Fz, Cz, Pz) were repeated measures. Main task effects were rendered meaningless, since amplitudes are scaled using within-task values, and analysis is focused exclusively on differences in the shape or pattern of wave amplitudes across electrode locations. A significant task by site interaction in scaled data is assumed to indicate an unconfounded difference in ERP amplitude distribution between the conditions (tasks) analyzed.

In Example 3, the ERP data was scaled within each condition (Truth and Malinger) and used ANOVAs to assess the possibility of distinct task-related scalp topographies. This analysis was done with both b-p and p-p amplitude data.

Re-analysis

In order to test the hypothesis that truth-telling and simulated amnesia may show distinct topographies in more than one type of memory task, scalp distribution data previously collected (but unanalyzed) were tested in a simple oddball task involving autobiographical memory. (i.e. not a P3FCP paradigm). Because the original design of the autobiographical study was between-groups, rather than within-subjects, slight modifications were made to the analysis. ERP amplitude data were vector length-scaled within the conditions of Truth (non-simulators) and Malinger (simulators), and tested using ANOVAs in which task was treated as a between-groups variable and site as a within subject repeated measure. This memory task (Birthday paradigm) consisted of the presentation of a series of dates, in which the subject's birthday was presented 11% of the time. Subjects were instructed to respond "yes" or "no" when asked if the date present was their birthday. Non-simulators were instructed to do their best, while simulators were instructed that they were to pretend they had suffered a head injury following which their memory was normal, but that they should fake the most severe memory deficit they could on the memory test, in order to obtain a fictitious insurance settlement.

Further Analysis

To assess topographical differences across paradigms, the experimental conditions Truth-P3FCP, Truth-Birthday, Malinger-P3FCP, and Malinger-Birthday were reconstructed using previously scaled b-p and p-p data from the Truth and Malinger conditions of both Birthday and P3FCP paradigms. Each data set was scaled within the appropriate condition in the respective paradigms for the previous analyses. A series of ANOVAs were then performed upon data in the following comparisons: Truth-P3FCP vs. Truth-Birthday (b-p and p-p), Malinger-P3FCP vs. Malinger-Birthday (b-p and p-p).

Results

Example 2

(Behavioral)

Table 3 shows that in the Truth blocks for all subjects, near 100% performance was obtained on average (2 of 25 subjects had one error each).

TABLE 3

Example 2 Behavioral Data

| Target % (block) | Mean % correct match (range) | Mean % correct mismatch (range) | Mean % incorrect match (range) | Mean % incorrect mismatch range) |
|---|---|---|---|---|
| 100 (Truth) | 99 (94–100) | 99 (98–100) | 0 (0–1) | 0 (0–1) |
| 85–90 (Malinger) | 79 (70–89) | 85 (77–88) | 21 (11–33) | 15 (8–28) |
| 75–80 (Malinger) | 65 (49–72) | 73 (60–84) | 35 (17–50) | 27 (18–34) |

In the 75–80% group, overall hit rate slightly undershot the target range at about 71%, as was the case in the 85–90% group where the overall hit rate was 84%. Within-subject 1-tests in both subject groups showed that overall hit rates differed between Truth and Malinger blocks. In the 85–90% group $t_{12}=9.18$, $p<0.001$, and in the 75–80% group, $t_{11}=16.35$, $p<0.001$. A between-subjects t-test also showed that the 75–80% and 85–90% groups had significantly different overall hit rates, $t_{23}=4.95$, $p<0.001$. Manipulation of simulated malingering hit rates was successful in this example.

ERP Group Effects (unscaled data)

There is little difference in P3 amplitude between Truth and Malinger conditions as is evident from Table 4, containing group b-p and p-p means. T-tests (as above) yielded insignificant ($p>0.3$) t-values on these amplitude values. These simulated malingering hit rate manipulations had no effect on P3 (recorded at Pz) in either amplitude, or in latency (t-tests yielded $p>0.3$).

TABLE 4

P3 amplitude and Latency-group means, Pz

| Target Group | b-p($\mu$V) | p-p($\mu$V) | latency (msec) |
|---|---|---|---|
| 100% | 8.1 | 11.7 | 560 |
| 85–90% | 7.3 | 10.5 | 603 |
| 75–80% | 7.3 | 11.8 | 532 |

ERP Individual Diagnostics

Independent measures t-tests within each subject were used to determine whether P3 amplitude match-mismatch differences at Pz were indicative of subjects' ability to discriminate. Table 5 contains the percentages of simulated malingerers in this study that were shown with these diagnostics to be able to discriminate matches and mismatches in the P3FCP.

TABLE 5

Individual correct diagnostic rates
(N of detected subjects) based on Pz P3 amplitude analysis

| Target Group | b-p | p-p |
|---|---|---|
| 100% | 28% (7 of 25) | 40% (10 of 25) |
| 85–90% | 23% (3 of 13) | 38% (5 of 13) |
| 75–80% | 38% (5 of 13) | 68% (9 of 13) |

With df=106, roughly 23% (b-p, 85–90% group) to 69% (p-p, 75–80% group) were shown to have t-values significant at the 0.05 level. Thus, although the group amplitude means did not differ significantly, the greatest proportion of subjects in the group (69%) doing the most malingering (75–80% hit rate) was detected using the p-p measure.

Example 2

(Behavioral)

As shown in Table 6, the behavioral hit rate manipulation apparently succeeded, with subjects slightly undershooting the Malinger target hit rate of 75% and scoring at about 70% correct.

TABLE 6

Example 2 Behavioral Data

| Target % (Truth or Malinger) | % Match Correct (range) | % Mismatch Correct (range) |
|---|---|---|
| Match Rare | | |
| 100 (Truth) | 95.9 (94–100) | 99.8 (99–100) |
| 75 (Malinger) | 69.6 (65–78) | 74.3 (62–80) |
| Match Frequent | | |
| 100 (Truth) | 99.7 (99–100) | 99.5 (99–100) |
| 75 (Malinger) | 73.6 (66–77) | 66.8 (56–80) |

A two-way ANOVA of task (two levels: Truth and Malinger) and match probability (Match Rare and Match Frequent) yielded only one significant effect on hit rates, that of task ($F_1=27.036$, $p<0.02$). The match probability ($F_{1,10}=0.01$, $p>0.9$) and the match probability X task interaction ($F_{1,10}=1.699$, $p>0.2$) effects were not significant.

ERP Group Analysis (unscaled data)

Match Probability and Task Effects

Figure 8:
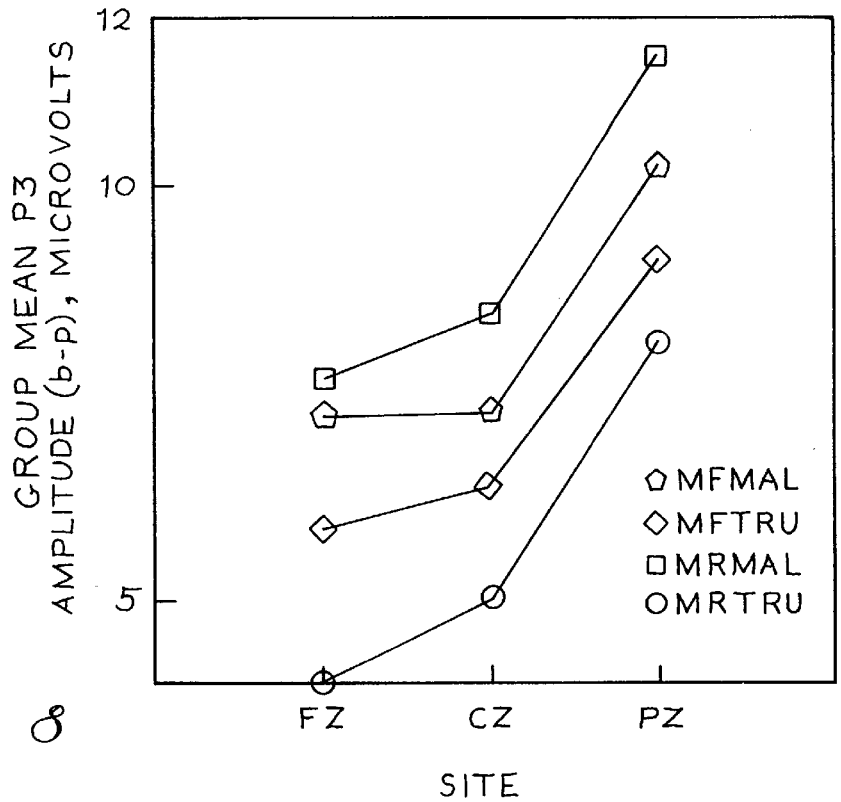
FIG. 8 is a diagram plotting group mean P3 amplitude (b-p), μV, P3FCP, where MRTRU=Match Rare, Truth; MRMAL=Match Rare, Malinger.

Initially investigated was the possible oddball type (i.e., match or mismatch) effect on P3 amplitude in the P3FCP. FIGS. 8 (b-p) and 9 (p-p) represent computer calculated, group mean unscaled P3 amplitudes in all conditions (Match Rare/Truth, Match Rare/Malinger, Match Frequent/Truth, Match Frequent/Malinger) at the three sites Fz, Cz, and Pz. Again, there is an apparent P3 amplitude difference between tasks (Truth and Malinger) in Match Rare data, which does not appear as pronounced in Match Frequent data. Three way within-subject repeated measures ANOVAs of match probability (two levels: Match Rare and Match Frequent), task (two levels: Truth and Malinger), and site (Fz, Cz, Pz) revealed significant task and site effects in the oddball b-p measure (task: $F_{1,10}=11.79$, $p<0.007$; site: $F_{2,20}=22.185$, $p<0.0001$) and the oddball p-p measure of amplitude (task: $F_{1,10}=20.115$, $p<0.002$; site: $F_{2,20}=32.791$, $p<0.0001$), and an absence of any main match probability effect ($p>0.4$ in both b-p and p-p data). The three-way interaction was also not significant in either case ($p>0.8$).

However in the p-p measure, both a significant match probability by site interaction ($F_{2,20}=4.599$, $p<0.05$, Greenhouse-Geiser corrected) and a marginal match probability by task interaction ($F_{1,10}=4.447$, $p<0.07$) resulted. The interactions were not observed in b-p data. This suggests that match probability may indeed have some effect on P3 amplitude in this paradigm, but only in interactions with other variables and in the P3 p-p index. The reduced task-related amplitude difference in Match Frequent data (see FIGS. 8 and 9) is consistent with these interactions.

These results suggest that the P3s elicited in the P3FCP by oddball match probes in simulated malingering subjects differs in overall mean amplitude from those in the Truth conditions. Also, as illustrated by FIGS. 10 and 11 and Table 7, this amplitude difference is: Malinger amplitude>Truth amplitude.

TABLE 7

Group mean P3 (at Pz) amplitude, $\mu V$

| Target %e (Truth or Malinger) | b-p | p-p |
|---|---|---|
| Match Rare | | |
| 100% (Truth) | 8.082 | 11.267 |
| 75% (Malinger) | 11.558 | 15.435 |
| Match Frequent | | |
| 100% (Truth) | 9.078 | 11.613 |
| 75% (Malinger) | 10.183 | 11.873 |

This is consistent with the finding in Example 2 that the rate of detection of malingering was greatest in the condition (75–80%) requiring the most malingering Task Effect Discussion It is important to note that in both Examples 2 and 3, match (oddball)-evoked P3 amplitudes were consistently larger than mismatch (frequent)-evoked P3 in both Truth (truth-telling) and Malinger (deceptive) conditions. As observed (See, Rogers. R., Harrel, E. H., & Liff, C. D. Feigning neuropsychological impairment: a critical review of methodological and clinical considerations. *Clinical Psychology Review,* 13, 255–274 (1993)), there is need for some non-behavioral means to evaluate the act of feigning in suspects, in combination with the evaluation of apparent cognitive abilities, in the field of malingering detection. In Example 2, this result enabled correct identification of up to 69% of simulators with a variety of behavioral scores (75% to 90% correct identification of matches and mismatches) that, while indicative of malingering, might not be conclusive in a field setting. It would appear difficult for a subject to sustain a claim of inability to discriminate matches and mismatches in the face of clear objective, quantitative data indicating that his brain can make this discrimination. The disagreement of the ERP-based index (intact ability to discriminate) with the behaviorally-based index of ability (impaired) to discriminate can serve as an indication of feigned impairment (i.e., amnesia).

Both Examples 2 and 3 results indicate that individuals simulating cognitive deficit on matching-to-sample tests show match-evoked P3 amplitudes at least as large as or larger than those evoked during honest performance. A dual-task reduction may have been expected (See, Kramer et al., above) in ERPs in the Malinger conditions because of the increased task complexity and possible cognitive demands associated with deceptive behavior, especially since it was revealed that subjects tracked their responding patterns as a simulation strategy. This could have created extra work and further diverted attentional resources from the primary task, (i.e., the FCP). This dual task reduction was apparently canceled to some extent in Example 2 by a reverse dual task effect (See, Kramer, A., Wickens, C., Vanasse, L., Heffley, E., & Conchin, E., Primary and secondary task analysis of step tracking: an event-related potentials approach in R. C. Sugarman (Ed.), *Proceedings of the 25th annual meeting of the Human Factors Society,* Rochester, N.Y., Rochester: Human Factors Society, (1981)); i.e., when a secondary task (malingering) shares relevant task attributes with and is embedded within the primary task (the FCP), P3 amplitude increases with task difficulty. Amnesia simulation may have required more attention from subjects to test stimuli than during Truth blocks, since not only were simulators required to respond to the stimuli, they also needed to selectively respond incorrectly in a subset of trials in a convincing enough manner to convey the impression of impairment.

Test stimuli were crucial for both the match-mismatch discrimination (the sole task in Truth blocks) and the added task of simulated malingering.

The expected dual task reduction also appears to have been avoided by the additional instruction of Example 3 subjects to not track their responding during testing. This apparently removed other aspects of the secondary task (i.e., selective incorrect responding) that were not relevant to the primary task. In other words, the decision to answer correctly or incorrectly shares the relevant characteristics of the primary task of identifying matches in the P3FCP but keeping a count of responses does not, and serves only to use attentional resources in a competitive rather than a facilitatory manner. This reverse dual task effect might therefore also help to account for the observed group effect where Malinger ERPs to oddball stimuli were larger than Truth ERPs in Example 3, as can be seen in FIGS. 8 and 9 (group mean unscaled P3 amplitudes in all conditions). Simulation research (used in nearly all research on feigned cognitive deficits) is based on an analog design in which normal subjects are given experimental instructions to simulate a mental impairment. Data is then compared with data from some control group (normal subjects or truly impaired individuals performing honestly). A drawback of this design is its unknown generalizability to actual malingerers in real-world settings (Rogers et al., 1993). With respect to field application, it seems advantageous that variable behavioral hit rates (70–90% correct) do not reduce oddball-evoked P3 amplitude or the statistical significance of oddball-frequent differences in our P3FCP. Indeed, as just noted, Examples 2 and 3 indicated that individuals simulating cognitive deficits showed match-evoked P3 amplitudes as large as (Example 2) or larger (Example 3) than those evoked during honest performance. This is an important observation, since it can be certain that there is variability in the response patterns of malingering individuals and no feasible way to predict precisely how a suspect may perform. A test that can be generalized across behavioral hit rates substantially greater than chance (50%) is one that can be used with some measure of confidence in a larger number of situations in the field.

Example 3
Scalp Amplitude Distribution Analysis
P3FCP Results

Further analyses was performed on Example 3 data to assess the possibility of different scalp amplitude topographies for each task. The analyses was restricted to Match Rare data. The group mean scaled values at each site(Fz, Cz, and Pz) for both Truth and Malinger conditions are represented in FIGS. 10 (b-p) and 11 (p-p), and there do appear to be different amplitude distributions for each task. ANOVA of scaled data revealed marginally significant interactions of task and site in both b-p ($F_2,20=3.824$, $p<0.04$, Greenhouse-Geiser corrected $p<0.07$) and p-p ($F_2,20=3.429$, $p<0.06$, Greenhouse-Geiser corrected $p<0.08$) amplitudes. This suggests distinct scalp topographies for Truth and Malinger conditions in the P3FCP. The use of greater numbers of subjects and sites in future studies may result in more robust effects.

Re-analysis

A series of P3-enhanced malingering detection paradigms, including the P3FCP had been previously published (See, Rosenfeld, et al. 1996, above). Ellwanger et al. (1996) used autobiographical information in a classic oddball task in a similar manner. Taking advantage of the fact that P3s in response to studied, recognized, or "old" items are larger than in response to novel items (See, Karis, D., Fabiani, M., & Donchin, E., 'P300' and memory: Individual differences in the von Restorff effect. *Cognitive Psychology* 16, 177–216 (1984)), it was predicted that P3s to the subject's own birthday (the oddball stimulus) embedded in a series other dates would also be larger in amplitude than to the frequent other dates. This knowledge recognition paradigm did indeed elicit larger amplitude P3s to the oddball autobiographical stimuli than to the novel, non-memory items in both simulators (Malinger condition) and non-simulators (Truth condition). A weighted average of behavioral responses (correct detection of one's own birthday, correct rejection of other dates) of both naive and sophisticated simulators shows that behavioral hit rates were higher (at 83% correct) than in the P3FCP (approximately 69% correct). Ellwanger et al. (1996) also detected an average of 88% of simulators using a modified bootstrap procedure on ERPs at Pz only. In the FCP data above, substantial Truth-Malinger amplitude differences are suggested, along with an apparent task by site interaction.

In the present re-analysis, the possibility was investigated that distinct P3 amplitude scalp topographies would also be seen in these data following scaling. This seemed a reasonable assumption since information transmission, stimulus probability, and stimulus complexity are all held constant across tasks while task complexity is manipulated, and this could conceivably alter P3 amplitude distribution between conditions.

Baseline-to-peak (b-p) data, only, was reported in these analyses. FIG. 13 (b-p) represents group mean scaled amplitudes at the midline three sites for Truth vs. Malinger groups. Again, as in the P3FCP data above, distinct distributions for each task are suggested. This was confirmed by ANOVA, in which the interaction of task and site was significant ($F_{2,70}=3.457$, $p<0.04$, Greenhouse-Geiser corrected $p<0.05$).

Further Analysis

Since evidence was found for distinct Malinger and Truth scalp P3 amplitude distributions in each of the above paradigms, it was considered if there might be a distinct Malinger scalp distribution that could be identified in both paradigms. Johnson's model (See, Johnson R. "On the neural generators of the P3000 component of the event-related potential" *Psychophysiology*, 30, 90–97 (1993)) predicts that different combinations of stimulus type and task will produce different distributions, and it was expected that evidence would be found for paradigm-related topographical differences. FIG. 14 (b-p) represents group mean scaled amplitudes in Truth conditions for both paradigms at each recording site. In FIG. 14 (showing mean scaled b-p amplitudes at Fz, Cz, and Pz, P3FCP vs. Birthday), distinct paradigm-related topographies are apparent. ANOVAs on scaled means of Truth-P3FCP vs. Truth-Birthday (see Methods) revealed a significant interaction of paradigm and site in b-p ($F_{2,44}=8.008$, $p<0.002$, Greenhouse-Geiser corrected $p<0.002$) data.

FIG. 15 (b-p) represents the group mean scaled amplitudes at Fz, Cz, and Pz for Malinger data from each paradigm, and visually there appears to be little indication of distinct paradigm-related topographies. Analysis failed to find significant task by site interactions in the b-p measure ($F_{2,66}=0.630$, $p=0.536$, Greenhouse-Geiser corrected $p=0.502$). These analyses (FIGS. 14 and 15) show a paradigm effect on distributions in the Truth but not in Malinger conditions. (Note that the two paradigms were not combined into a three-way ANOVA, since one paradigm involved within-subjects and the other, between-groups).

Topography Discussion

Considerable diversity may exist in P3 scalp topography as a function of experimental values. Preliminary evidence was found that for distinct task-related topographies in both the matching-to-sample and autobiographical oddball paradigms. The possibility was considered the Malinger condition represented a more demanding, more complex task than that of honest responding, since simulators are required to modify their behavioral responses so as to appear cognitively impaired. A differential level of task complexity may account for the distinct Truth-Malinger topographies due to possibly differential activation of putative neural generators that govern processing of the task complexity-related variables. This is consistent with the position that in any given situation, the total number and configuration of active processors/generators depends on the nature of the stimulus information and the subject's task, the effects of each on P300 amplitude will have its own characteristic scalp distribution.

However, upon closer examination of FIGS. 10 (P3FCP) and 13 (Birthday), it appears that in the P3FCP, the mean scaled amplitude increases at Cz and decreases at Pz in the Malinger condition relative to Truth, while in the Birthday task Cz mean scaled amplitude decreases and Pz increases (relative to other recording sites) between Truth and Malinger conditions. FIG. 16 (b-p) combines Truth and Malinger scaled amplitude from both these paradigms, and it can be seen that the Truth topographies (dark traces) are more different looking than the Malinger distributions, which was also confirmed statistically. While the actual amplitude change between Truth and Malinger topographies may be different between the P3FCP and Birthday paradigms (i.e., in the P3FCP paradigm, Cz amplitude increases and in the Birthday paradigm Cz amplitude decreases, etc.), the act of malingering appears to bring the P3 distributions toward some common shape across paradigms.

Because each paradigm involves different stimulus types (three-digit numbers vs. calendar dates) and tasks (matching-to-sample vs. recognition of autobiographical information), and slightly different subjective probabilities (17% vs. 11%), it was expected that their scalp topographies would be correspondingly different in the Truth conditions. Since the Truth conditions consist of only the primary tasks (matching to sample or birthday recognition), there are mainly the paradigm-specific effects operating. However, in the Malinger condition, another task, that of selective incorrect responding so as to simulate cognitive deficit, is added. Whether it is merely the increased complexity and demands inherent in the attempt to successfully malinger amnesia, or something specific to the act or awareness of deception itself, some characteristic of this secondary task (amnesia simulation) affects scalp P3 topographies regardless of the primary paradigm. This might account for the lack of evidence for distinct paradigm-related distributions in Malinger conditions in our analyses.

Alternative Embodiments

Various alternative embodiments may be utilized to obtain a scaled amplitude distribution indicative of deception. The following alternative is particularly suitable for an interrogation.

A subject to be interrogated is coupled to the appropriate brain wave sensing equipment as discussed above. The electrodes are connected to the appropriate scalp sites in order to obtain a topographic distribution from two or more sites, as described above. A series of tones are presented to the subject. Most of the tones (e.g. 80%) are of the same pitch, but a small percentage (e.g. 20%) of the tones are at a distinctively different pitch. Since these are rare and task-relevant (e.g., by having a subject press a button each time one is presented), each rare tone will evoke the P300 ERP. The subject's P300 distribution is measured and recorded in response to the presentation of each of the rarer tones.

The subject is then interrogated. The interrogation may be arranged in various different ways. In one way, the subject is presented with a series of questions to which he is required to provide answers. The questions may be prepared to include questions to which the subject is known to have knowledge, questions to which the subject is known not to have knowledge, as well as questions to which it is not known whether the subject has knowledge. Shortly after the time that the subject provides the required response to each question, he is also presented with one of the two tones. The subject's P300 brain wave amplitude distribution is also obtained when the subject's verbal response it being provided.

The analysis of the subject's ERP topographic response can be used as an indication of deception. More specifically, the suspect is first given a simple, two tone oddball paradigm, yielding (as above) a control (C) distribution of scaled P300 amplitude. This is compared with the test (T) distribution during interrogation. Again, it is first necessary to determine what the normative/standard distribution in innocent truth-tellers or non-malingerers, during interrogation, looks like. The average difference between this distribution and the distribution (in the same honest subjects) in the simple two tone paradigm, can be used to correct the C-distributions in suspects in the field, as noted above with respect to autobiographical and match-to sample paradigms). However, the scaled amplitude distribution in response to the oddball tones when the subject is responding deceptively should be different compared to the scaled amplitude distribution of the subject to the oddball tones when the subject is not responding. This type of interrogation is effective since the mental activity of the subject required for deception affects the subject's oddball response to the presentation of the rare tones. Various other interrogation paradigms may be utilized following these general techniques.

In some of the above embodiments, deception on the part of the subject was detected by using a comparison based on bootstrapped distributions for the two profiles, and performing an analysis of variance on the bootstrapped data. Other kinds of statistical methods may be used to make the comparison between the scaled distribution to the control stimulus and the scaled distribution to the test stimulus. For example, instead of using the ANOVA technique, described above, a cross correlation technique could be used. Cross correlation techniques are well known to investigators and are commonly used to compare one distribution to another. Cross correlation can be used in any of the embodiments described above to compare the scaled amplitude distributions of the subject to obtain an indication of deception.

Summary and Conclusions

Various aspects of P3-enhanced malingered amnesia detection were analyzed in the above described examples. First, it was demonstrated that it is indeed possible to manipulate individuals toward a given behavioral hit rate and that these variable rates do not appear to attenuate the oddball-evoked P3 during this matching-to-sample task. Also, the match-evoked P3 amplitudes were larger than mismatch-evoked amplitudes in both Malinger and Truth conditions. There was no evidence of dual task reduction since the oddball P3 in simulators was as large as or larger than that in nonsimulators (Examples 2 and 3). However, indications were found of a task-related effect on P3 amplitude between Truth and Malinger conditions, in both the analyses of unscaled data, and in the distinct Truth and Malinger scaled scalp topographies in Example 3. While no main effect was found for whether oddballs in the P3FCP were matches or mismatches to their respective samples, it can be seen in FIGS. 8 and 9 (group mean b-p and p-p amplitudes at Fz, Cz, and Pz) that the Truth-Malinger amplitude difference was more pronounced in Match Rare than Match Frequent data. In a given suspect situation in which an individual performs at an ambiguous behavioral rate (at or greater than chance) that may be suggestive of malingering, but the diagnosis cannot be made with absolute certainty, the second involuntary indicator (the increased P3 amplitude to all oddball match probes, including those to which the suspect incorrectly responds) can help validate the suspicion of feigning.

In the re-examination of previous study's Birthday task data, distinct Truth-Malinger unscaled amplitude differences were found as illustrated in FIG. 12. The topographical analysis found additional evidence for a task-related amplitude profile effect in the form of distinct scalp amplitude distributions for Truth and Malinger conditions. Comparing these data with those from the P3FCP also gave preliminary evidence for activity of neural generators involved in the processing of task complexity variables. These activities not only produce distinct Truth and Malinger topographies within each individual paradigm, but may also bring about a common distribution across paradigms when the secondary task of deception is involved.

Clearly, there is evidence for Truth-Malinger topographical differences in at least two P3-enhanced malingering detection paradigms. In alternative embodiments, such topographical differences may also be utilized in other types of detection paradigms, utilizing, for example, verbal information as stimuli, rather than numerical or autobiographical information. However, this pattern of response may not be due to deception per se, but is might be related to the additional cognitive and/or emotional demands (task complexity) associated with deception.

It is intended that the foregoing detailed description be regarded as illustrative rather than limiting and that it is understood that the following claims including all equivalents are intended to define the scope of the invention.

I claim:

1. A system for detecting untruthfulness in a subject comprising:

equipment for administering one or more testing sessions, each of said one or more testing sessions comprising presenting at least one test to the subject and obtaining a reply to said at least one test from the subject the untruthfulness of which is to be determined;

sensing equipment responsive to brain waves from at least two locations of a subject's scalp and producing output signals indicative thereof, each of said output signals having a peak amplitude associated with each reply; and analysis equipment including a program responsive to said output signals for generating a test profile representing the relationship between said peak amplitudes sensed at said at least two locations for each reply and comparing said test-profile to a previously obtained control profile for which truthfulness by the subject has been established.

2. The system of claim 1 wherein said testing session comprises:

a series of tests, wherein in each of said tests the subject is required to provide a reply; and wherein a profile of the subject's brain waves is obtained during each of said tests.

3. The system of claim 1 wherein said testing session comprises:

a presentation to the subject of a control sample stimulus about which the subject is known to be familiar;

and wherein said program determines a control profile from the output signals from said sensing equipment associated with said presentation of said control sample stimulus to thereby provide said previously obtained control profile for which truthfulness has been established.

4. The system of claim 1 wherein said test profile and said control profile each represent a scaled distribution of said output signals.

5. The system of claim 1 wherein said sensing equipment is responsive to brain waves from at least three locations.

6. The system of claim 1 wherein said analysis equipment further comprises means for calculating a bootstrapped distribution of said output signals and means for determining an analysis of variance on the means of said bootstrapped distributions between the control profile and the test profile of said output signals associated with said reply.

7. The system of claim 1 wherein said sensing equipment is responsive to P300 brain waves.

8. The system of claim 1 wherein said testing session comprises:

a presentation of a sample stimulus; and a presentation of the test, said test comprising a test stimulus;

and wherein said reply comprises an indication by the subject whether said test stimulus matches said sample stimulus.

9. The system of claim 1 wherein said testing session comprises:

a presentation of a sample stimulus; and a presentation of a test, said test comprising presentation of a plurality of test stimuli wherein at least one of said test stimuli matches said sample stimulus and wherein at least one of said test stimuli does not match said sample stimulus;

and wherein said reply comprises an indication on the part of the subject whether said test stimulus matches said sample stimulus.

10. The system of claim 9 wherein said at least one of said test stimuli matching said sample stimulus is presented infrequently enough to produce an oddball effect.

11. The system of claim 1 further comprising:

acquisition of the control profile by presentation of a plurality of stimuli including control stimuli about which the subject is known to be familiar, obtaining P300 brain waves of the subject at said at least two locations in response to said control stimuli, and generation of a profile thereof.

12. A method for detecting untruthfulness in a subject, said method comprising the steps of:

presenting a trial to a subject;

during said trial, obtaining brain wave measurements from at least two scalp sites of the subject;

calculating a peak amplitude for each brain wave measurement from each site;

generating a profile representative of the relationship between said peak amplitudes from the at least two sites; and comparing said profile of said brain wave measurements to a profile for which truthfulness has been established.

13. The method of claim 12 further comprising:

presenting a series of tests, wherein in each of said tests the subject is required to provide a reply to a test stimulus; and obtaining a profile representing the relative amplitudes for the amplitude distribution of the subject's brain waves from said at least two sites during each of said series of tests.

14. The method of claim 12 further comprising:

presenting to the subject a control sample stimulus about which the subject is known to be familiar; and obtaining brain wave measurements from said at least two scalp sites of the subject in response to presentation of said control sample; and determining a control profile representing a comparison of the amplitude distribution from the brain wave measurements obtained from said at least two sites in response to said presentation of said control sample.

15. The method of claim 14 further comprising:

comparing said profile of said brain wave measurements to said control profile.

16. The method of claim 12 wherein said trial requires the subject to provide a reply to a test stimulus.

17. The method of claim 12 wherein said step of comparing further comprises determining a scaled distribution of said brain wave measurements from the at least two sites.

18. The method of claim 12 wherein said step of comparing further comprises calculating a bootstrapped distribution of said brain wave measurements and determining an analysis of variance on the means of said bootstrapped distributions between the profile of said brain wave measurements for which truthfulness had been established and the profile of said brain wave measurements from the at least two sites obtained during the trial.

19. The method of claim 12 wherein said step of comparing further comprises performing a cross correlation analysis between the profile of said brain wave measurements for which truthfulness had been established and the profile of said brain wave measurements from the at least two sites obtained during the trial.

20. A system for determining truthfulness of a subject and having sensing equipment responsive to brain waves from at least two scalp sites of the subject and a test session in which the subject replies to a presentation of a test stimulus, the system comprising:

means for obtaining a control profile representing P300 responses of a subject at a plurality of scalp sites;

means for presenting the subject with a plurality of trials;

means for obtaining a response profile of the subject representing P300 responses of the subject at said plurality of scalp sites to said plurality of trials; and means for comparing said response profile to said control profile as an indicator of truthfulness.

21. The system of claim 20 wherein said presenting means further comprises means for presenting a series of trials wherein at least some trials of said series of trials present information about which the subject is unfamiliar and other trials of said series of trials present information about which the subject's familiarity is subject to detection for deception.

22. The invention of claim 1 wherein said test profile and said control profile each represent an amplitude independent distribution of said output signals.

23. The method of claim 12 wherein the comparing step further comprises an amplitude independent comparison of said brain wave measurements from the at least two sites.

24. The system of claim 20 wherein said response profile and said control profile each represent amplitude independent distributions of said P300 responses.

25. The system of claim 20 wherein said response profile and said control profile each represent a vector length scaled distribution of said P300 responses.

26. A method for detecting untruthfulness in a subject, said method comprising the steps of:

presenting a trial to a subject;

during said trial, obtaining brain wave measurements from at least two scalp sites of the subject;

calculating a peak amplitude for the brain wave measurements from each site;

generating a curve from said peak amplitudes from the at least two sites, said curve representing a test profile of said brain wave measurements; and comparing said test profile curve of said brain wave measurements to a similarly obtained control profile curve for which truthfulness has been established.

27. The method of claim 26 wherein said comparing step further includes the step of comparing the shapes of said test profile and said control profile.

28. The method of claim 26 further comprising the step of normalizing said brain wave measurements from the at least two sites.

29. The method of claim 28 wherein said normalizing step further includes the step of vector length scaling said brain wave measurements from the at least two sites.

30. The method of claim 26 further comprising:

presenting a series of tests, wherein in each of said tests the subject is required to provide a reply to a test stimulus; and generating a curve representing a test profile from the amplitude distribution of the subject's brain waves from said at least two sites during each of said series of tests.

31. The method of claim 26 further comprising:

presenting to the subject a control sample stimulus about which the subject is known to be familiar; and obtaining brain wave measurements from said at least two scalp sites of the subject in response to presentation of said control sample; and generating a curve representing a control profile from the amplitude distribution of the brain wave measurements obtained from said at least two sites in response to said presentation of said control sample.

32. The method of claim 31 further comprising:

comparing said test profile of said brain wave measurements to said control profile.

33. The method of claim 26 wherein said trial requires the subject to provide a reply to a test stimulus.

34. The invention of claim 26 wherein said step of comparing further comprises determining a scaled distribution of said brain wave measurements from the at least two sites.

35. The method of claim 26 wherein said step of comparing further comprises calculating a bootstrapped distribution of said brain wave measurements and determining an analysis of variance on the means of said bootstrapped distributions between the control profile of said brain wave measurements for which truthfulness had been established and the test profile of said brain wave measurements from the at least two sites obtained during the trial.

36. The method of claim 26 wherein said step of comparing further comprises performing a cross correlation analysis between the control profile of said brain wave measurements for which truthfulness had been established and the test profile of said brain wave measurements from the at least two sites obtained during the trial.

37. The system of claim 1 wherein said relationship is a curve.

38. The system of claim 1 wherein said relationship is a iso-potential map.

39. The method of claim 12 wherein said step of generating further comprises the step of generating a curve.

40. The method of claim 12 wherein said step of generating further comprises the step of generating a iso-potential map.

* * * * *

UNITED STATES PATENT AND TRADEMARK OFFICE
CERTIFICATE OF CORRECTION

PATENT NO.  : 5,957,859
DATED       : September 28, 1999
INVENTOR(S) : J. Peter Rosenfeld It is certified that error appears in the above-identified patent and that said Letters Patent is hereby corrected as shown below:

In the Claims

In claim 20, line 6, after "representing" insert --the--.

In claim 20, line 10, after "representing" insert --the--.

Signed and Sealed this

Twenty-ninth Day of May, 2001

Attest:

NICHOLAS P. GODICI

*Attesting Officer*    *Acting Director of the United States Patent and Trademark Office*